United States Patent
Connolly

(10) Patent No.: US 12,196,764 B2
(45) Date of Patent: Jan. 14, 2025

(54) ANALYSIS TECHNIQUES FOR MEASURING GLYCATED HEMOGLOBIN IN UNDILUTED BLOOD SAMPLES

(71) Applicant: Jim Connolly, Indianapolis, IN (US)

(72) Inventor: Jim Connolly, Indianapolis, IN (US)

(*) Notice: Subject to any disclaimer, the term of this patent is extended or adjusted under 35 U.S.C. 154(b) by 675 days.

(21) Appl. No.: 17/523,113

(22) Filed: Nov. 10, 2021

(65) Prior Publication Data

US 2022/0065876 A1  Mar. 3, 2022

Related U.S. Application Data

(62) Division of application No. 15/820,611, filed on Nov. 22, 2017, now Pat. No. 11,199,551.

(51) Int. Cl.
| | | |
|---|---|---|
| G01N 33/72 | (2006.01) | |
| A61B 5/145 | (2006.01) | |
| A61B 5/15 | (2006.01) | |

(52) U.S. Cl.
CPC ....... *G01N 33/726* (2013.01); *A61B 5/14532* (2013.01); *A61B 5/14535* (2013.01); *A61B 5/150358* (2013.01); *G01N 33/723* (2013.01)

(58) Field of Classification Search
CPC ................ G01N 33/723; G01N 33/726; A61B 5/14532; A61B 5/14535; A61B 5/150358
See application file for complete search history.

(56) References Cited

U.S. PATENT DOCUMENTS

| | | |
|---|---|---|
| 4,876,205 A | 10/1989 | Green et al. |
| 6,127,138 A | 10/2000 | Ishimaru et al. |
| 6,392,209 B1 | 5/2002 | Oppitz |
| 6,475,360 B1 | 11/2002 | Hodges et al. |
| 6,632,349 B1 | 10/2003 | Hodges et al. |
| 7,306,283 B2 | 12/2007 | Howick et al. |
| 7,330,283 B2 | 2/2008 | Lee et al. |
| 7,491,310 B2 | 2/2009 | Okuda et al. |
| 7,749,764 B2 | 7/2010 | Su et al. |
| 8,460,524 B2 | 6/2013 | Popovich et al. |
| 8,603,309 B2 | 12/2013 | Cai et al. |
| 8,673,646 B2 | 3/2014 | Yuan et al. |

(Continued)

FOREIGN PATENT DOCUMENTS

| | | |
|---|---|---|
| EP | 0313390 A2 | 4/1989 |
| EP | 1693461 A1 | 8/2006 |

(Continued)

OTHER PUBLICATIONS

European Patent Office "Communication pursuant to Article 94(3) EPC", European Patent Office, Application No. 18 815 865.3, Jun. 22, 2023, 4 pages.

(Continued)

*Primary Examiner* — Robert J Eom
(74) *Attorney, Agent, or Firm* — Blanchard Horton PLLC

(57) ABSTRACT

Electrochemical test sensors and analysis methods are described that reduce or eliminate the pre-treatment or dilution of blood samples prior to HbA1c analysis. Thus, a blood sample obtained from a blood draw or phlebotomy may be introduced to the electrochemical test sensor for HbA1c analysis. The described test sensors immobilize or deactivate incompatible reagents, enzymes, and antibodies so they do not substantially interfere with each other during the analysis. The test sensors also use heat to catalyze reactions that otherwise would proceed at too slow of a rate to be practical.

22 Claims, 11 Drawing Sheets

(56) References Cited

U.S. PATENT DOCUMENTS

| | | |
|---|---|---|
| 8,815,076 B2 | 8/2014 | Cardosi et al. |
| 2004/0063213 A1 | 4/2004 | Hirai et al. |
| 2005/0019488 A1 | 9/2005 | McCabe et al. |
| 2005/0195488 A1 | 9/2005 | McCabe et al. |
| 2007/0000780 A1 | 1/2007 | Oya et al. |
| 2007/0242111 A1 | 10/2007 | Pamula et al. |
| 2009/0000947 A1 | 1/2009 | Akahori et al. |
| 2009/0009062 A1 | 4/2009 | Chuang et al. |
| 2009/0090623 A1 | 4/2009 | Chuang et al. |
| 2010/0025264 A1 | 2/2010 | Yuan et al. |
| 2011/0102127 A1 | 5/2011 | Schultes et al. |
| 2011/0172750 A1 | 7/2011 | Cassidy et al. |
| 2012/0261257 A1 | 10/2012 | Vanjari et al. |
| 2013/0010826 A1 | 1/2013 | Le Neel et al. |
| 2013/0193384 A1 | 8/2013 | Dorfman |
| 2014/0051159 A1 | 2/2014 | Bergstedt et al. |
| 2015/0226689 A1 | 8/2015 | Semancik et al. |
| 2016/0131537 A1 | 5/2016 | Aliane et al. |
| 2016/0279639 A1 | 9/2016 | Kim et al. |
| 2018/0163184 A1 | 6/2018 | Huang et al. |
| 2019/0154619 A1 | 5/2019 | Connolly |
| 2019/0317039 A1 | 10/2019 | Connolly |
| 2021/0310980 A1 | 10/2021 | Connolly |

FOREIGN PATENT DOCUMENTS

| | | |
|---|---|---|
| EP | 1914315 A1 | 4/2008 |
| EP | 1693461 B1 | 5/2011 |
| EP | 2568281 A1 | 3/2013 |
| JP | 03166701 A | 7/1991 |
| JP | 2006061019 A | 3/2006 |
| JP | 2009171874 A | 8/2009 |
| KR | 500009257 | 8/1995 |
| WO | 9940411 A1 | 8/1999 |
| WO | 2013153406 A1 | 10/2013 |
| WO | 2016038526 A1 | 3/2016 |
| WO | 2017038956 A1 | 9/2017 |

OTHER PUBLICATIONS

European Patent Office, "Communication pursuant to Article 94(3) EPC", European Patent Office, Application No. 18 815 882.8, Jul. 3, 2023, 6 pages.

"International Search Report and Written Opinion received for PCT Patent Application No. PCT/US2018/061722, mailed on Mar. 22, 2019", 6 Pages.

"International Search Report and Written Opinion received for PCT Patent Application No. PCT/US2018/061995, mailed on Mar. 11, 2019", 19 Pages.

"International Search Report and Written Opinion received for PCT Patent Application No. PCTUS2018060979, mailed on Feb. 12, 2019", 17 pages.

"Neutral Proteinase from *Bacillus* sp.", Toyobo Enzymes, Industrial Grade, Toyobo USA, Inc., New York, 285-287.

Ar-Rawi, A. H., et al., "Novel idea to monitor and measure blood hemoglobin noninvasively", African Journal of Biotechnology vol. 9 (54), pp. 9295-9306, Dec. 27, 2010. Available online at http://www.academicjournals.org/ AJB ISSN 1684-5315 © 2010 Academic Journals, Dec. 27, 2010, 9295-9306.

Baldwin, Richard P., et al., "Catalytic Reduction of Myoglobin and Hemoglobin at Chemically Modified Electrodes Containing Methylene Blue", Analytical Chemistry, vol. 60, No. 20, Oct. 15, 1988, Oct. 15, 1988, 2263-2268.

Chawla, et al., "An Amperometric Hemoglobin A1c Biosensor Based on Immobilization of Fructosyl Amino Acid Oxidase onto Zinc Oxide Nanoparticles—Polypyrrole Film", Analytical biochemistry, 430(2), 2012, 156-162.

Taylor, John Fuller, et al., "System Methemoglobin-Hemoglobin Potentials of The", J. Biol. Chem. 1939, 131:649-662., Oct. 4, 1939, 649-662.

Treo, Ernesto F., et al., "Comparative Analysis of Hematocrit Measurements by Dielectric and Impedance Techniques", IEEE Transactions on Biomedical Engineering, vol. 52, No. 3, Mar. 2005., Mar. 31, 2005, 549-552.

ANALYSIS TECHNIQUES FOR MEASURING GLYCATED HEMOGLOBIN IN UNDILUTED BLOOD SAMPLES

REFERENCE TO RELATED APPLICATIONS

This application is a division of U.S. Nonprovisional application Ser. No. 15/820,611, filed Nov. 22, 2017, entitled "Test Sensors, Systems, and Analysis Techniques for Measuring Glycated Hemoglobin in Undiluted Blood Samples," the contents of which are incorporated herein by reference in their entirety.

BACKGROUND

HbA1c is a stable glycated hemoglobin derivative that reflects the average blood glucose level over the preceding 2-3 months of a mammal. Thus, HbA1c (%-A1c) is a reflection of the state of glucose control in diabetic patients, providing insight into the average glucose control over the two to three months preceding the test. As such the HbA1c level in a blood sample provides an accurate index for average blood glucose level in the bloodstream of the mammal over an extended period of time. For diabetic individuals, an accurate measurement of %-A1c assists in the determination of the blood glucose level, as adjustments to diet and/or medication are based on these levels. Traditionally, clinical laboratory assays for HbA1c were obtained by ion-exchange chromatography, electrophoresis, immunochemical methods, and boronate affinity chromatography.

The majority of the glycated hemoglobin (HbA1c) measurement methods currently in use are based on pretreatment or dilution of a whole blood sample. One conventional method that is not is an optical system using reflectance in a laminar flow system that determines the concentration of A1c hemoglobin in blood. These systems use immunoassay chemistry where the blood is introduced to the test sensor where it reacts with reagents and then flows along a reagent membrane. When contacted by the blood, A1c antibody coated color beads release and move along with the blood sample to a detection zone. Because of the competition between the A1c in the blood sample and an A1c peptide present in the detection zone for the color beads, the color beads not attached to the A1c antibody are captured at the detection zone and are thus detected as the A1c signal from the change in reflectance. The total hemoglobin (THb) in the blood sample also is reacting with other blood treatment reagents and moves downstream into a different detection zone, where it is measured at a different wavelength. For determining the concentration of A1c in the blood sample, the reflectance signal is proportional to the A1c analyte concentration (% A1c). For the THb measurement, however, the reflectance in the different detection zone is inversely proportional to the THb (mg/dL) for the detection system. However, optical systems of this type tend to be less accurate that electrochemical systems.

Due to the expense, labor intensiveness, and time requirement, traditional HbA1c clinical laboratory assays have limited availability. While portable, the laminar flow optical systems tend to lack the desired accuracy and reproducibility of electrochemical systems. Thus, there is an ongoing need for simple and efficient electrochemical test sensors, systems, and analysis methods for determining the HbA1c content of a blood sample. The present invention avoids or ameliorates at least some of the disadvantages of traditional, analysis-laboratory-based and optical HbA1c analysis devices and methods.

SUMMARY

In one aspect, the invention provides a multi-analysis path test sensor for determining a glycated hemoglobin concentration of an undiluted blood sample, the test sensor including an inlet in fluid communication with a divided flow inlet and a common flow inlet, the divided flow inlet in fluid communication with at least one first isolated flow path and the common flow inlet in fluid communication with at least a second and a third isolated flow path; a hematocrit flow path in fluid communication with the divided flow inlet, the hematocrit flow path including at least four electrical conductors sequentially arranged in the first isolated flow path; a total hemoglobin analysis path in fluid communication with the common flow inlet, the hemoglobin analysis path including a total hemoglobin working and counter electrode pair arranged in the second isolated flow path; and a glycated hemoglobin analysis path in fluid communication with the common flow inlet, the glycated hemoglobin analysis path including a second chemical reaction zone, a pH adjustment zone, and a glycated hemoglobin working and counter electrode pair arranged in the third isolated flow path.

In another aspect of the invention, there is a method of determining a corrected glycated hemoglobin concentration of an undiluted blood sample, the method includes introducing an undiluted blood sample to a test sensor; applying a potential to at least two electrical conductors of a hematocrit flow path; determining an output current responsive to a hematocrit content of the sample; applying a potential to a total hemoglobin working and counter electrode pair; determining an output current from the total hemoglobin working and counter electrode pair responsive to a total hemoglobin concentration of the sample; applying a potential to a glycated hemoglobin working and counter electrode pair; determining an output current from the glycated hemoglobin working and counter electrode pair responsive to a glycated hemoglobin concentration of the sample; and determining a corrected glycated hemoglobin concentration of the sample from the output currents. The output currents are determined from the hematocrit flow path, the total hemoglobin working and counter electrode pair, and the glycated hemoglobin working and counter electrode pair.

In another aspect of the invention, there is a method of deactivating a lysing reagent and a protein cleaving reagent in a sample before contacting an enzyme with the sample, the method including after contacting a sample with a lysing reagent, contacting the sample with an interference reduction matrix, where the lysing reagent resides on a first side of a web and the interference reduction matrix resides on a second side opposite the first side; and after contacting the sample with a protein cleaving reagent, contacting the sample with a pH adjustment zone that substantially reduces the activity of the protein cleaving reagent Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. In the accompanying drawings and illustrations, the sizes and relative sizes, shapes, and qualities of lines, entities, and regions may be exaggerated for clarity. The components in the figures are not necessarily to scale and are not intended to accurately represent molecules or their interactions, emphasis instead being placed upon illustrating the principles of the invention.

DETAILED DESCRIPTION

Electrochemical test sensors and analysis methods are described that reduce or eliminate the pre-treatment or dilution of blood samples prior to HbA1c analysis. Thus, a blood sample obtained from a blood draw or phlebotomy may be introduced to the electrochemical test sensor for HbA1c analysis. The described test sensors immobilize or deactivate incompatible reagents, enzymes, and antibodies so they do not substantially interfere with each other during the analysis. The test sensors also use heat to catalyze reactions that otherwise would proceed at too slow of a rate to be practical.

The test sensors include an analysis path to quantify hematocrit (Hct) and/or blood sample viscosity, an analysis path to quantify total hemoglobin (THb), and at least one analysis path to quantify glycated hemoglobin (HbA1c). Additional analysis paths may quantify background or interferent responsive components in the HbA1c output current measured from the test sensor by quantifying the current obtained from the blood sample without the presence of the HbA1c responsive enzyme. Background channels may be provided that quantify the background current after lysing and cleavage of the blood sample and after lysing and reaction with an HbA1c specific enzyme. While not required, the described test sensors and analysis methods can analyze an undiluted blood sample for HbA1c after insertion of the test sensor into the measurement device in a time period from 20 to 400 seconds, preferably in a time period from 30 to 300 seconds, and more preferably in a time period from 40 to 220 seconds. At present, an especially preferred analysis time is from 120 to 200 seconds.

Figure 1:
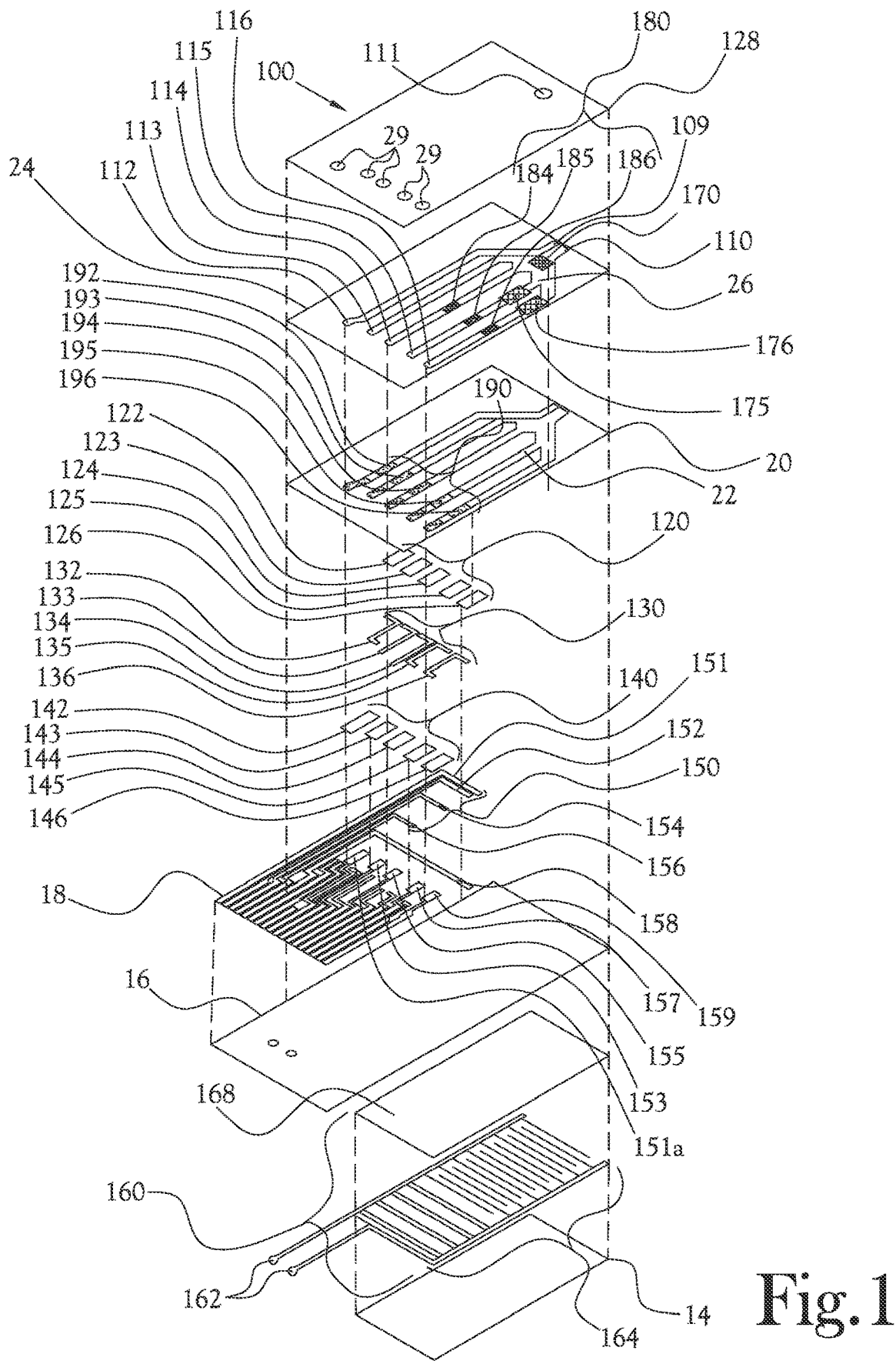
FIG. 1 is a vertically exploded view of a five-analysis-path test sensor.

FIG. 1 is a vertically exploded view of a five-analysis-path test sensor 100. The test sensor 100 preferably is formed in the general shape of a rectangle; however, other shapes consistent with the desired operation of the test sensor 100 may be used. The test sensor 100 may be produced from rolls of material that are sufficiently flexible for roll processing, but which are still rigid enough to give a useful stiffness to finished test sensor 100. The test sensor includes at least two chemical reaction zones and at least three electrical reaction zones.

Test sensor 100 includes an electrode support substrate 16, electrical conductors 18 positioned on the electrode support substrate 16, and a dielectric 20 on the electrical conductors 18. Dielectric 20 includes channels 22 exposing desired portions of the electrical conductors 18. Spacer 24 is positioned on the dielectric 20 and has openings 26 aligned with the channels 22. A cover 128 is on the spacer 24. The cover 128 includes vents 29 for each of the openings 26 and an inlet.

In combination, these elements form the test sensor 100 having at least one divided flow inlet 109 and a common flow inlet 110 that form five isolated flow paths 112, 113, 114, 115, 116. The divided flow inlet 109 continues to form the isolated flow path 112. The common flow inlet 110 branches to form the isolated flow paths 113-116. Thus, four isolated flow paths are formed from the common flow inlet 110 and a single isolated flow path is formed from the divided flow inlet 109. In this way, one or more of the isolated flow paths may be separated at or near the point the sample enters the test sensor 100, while two or more of the isolated flow paths branch from the common flow inlet 110 to form the remaining isolated flow paths.

For the test sensor 100, a liquid sample entering the inlet 111 of the test sensor 100 divides between any of the divided flow inlets 109 and the common flow inlet 110 before branching from the common flow inlet 110 into a total of five isolated flow paths 112-116, while air is vented from each flow path through the vents 29 in the cover 128. The liquid sample is bounded at the top by the underside of the cover 128, at the bottom by the electrical conductors 18 and the top of the electrode support substrate 16 and on the sides by the spacer 24 and the dielectric 20. While the isolated flow paths 112-116 are represented in a specific sequential order on the test sensor 100, the isolated flow paths 112-116 may be placed on the test sensor 100 in any order compatible with the desired electrical connections to a measurement device and analysis. Thus, other orientations of the isolated flow paths 112-116 on the test sensor 100 may be used.

The cover 128 is on the spacer 24. The cover 128 provides the top of the five isolated flow paths 112-116 in addition to providing the inlet 111 and the vents 29. The cover 128 may be formed from a polymeric material that has suitable flexibility for the manufacturing process. One such polymeric material is polyester. A preferred polyester is polyethylene terephthalate (PET), such as 90128 (HY-9 hot-melt adhesive on 5-mil PET) available from Adhesives Research, Inc., Pennsylvania, USA. Other polymeric materials may be used to form the cover 128 that provide the desired physical characteristics to the test sensor 100 and are compatible with the chemistry of the analysis.

The spacer 24 is on the dielectric layer 20. Channels in the spacer assist in forming the sides of the divided flow inlet 109, the common flow inlet 110, and the five isolated flow paths 112-116. The spacer 24 is preferably hydrophilic and may be formed from a flexible polymer, such as polyester or polyamide with an adhesive coating. One suitable polymer material for the spacer 24 is Airflow 90128 from Adhesive Research, York, Pa. The spacer 24 also may be formed through screen printing. Thus, one or more passes of a dielectric material may be screen printed to form the spacer 24. The spacer 24 also may be formed by cutting the channels into polymer/adhesive sheets with a laser. Finished sheets may then be laminated to the dielectric layer 20. The thickness (height) of the spacer 24 is chosen to provide the desired volume and sample capillary flow from the inlet 111 to the electrodes of the five isolated flow paths 112-116. For example, the thickness of the spacer 24 may be from 51 micrometers (um) to 178 um.

The dielectric layer 20 is on the electrical conductors 18 and the electrode support substrate 16. The dielectric layer 20 prevents the liquid sample from contacting undesired portions of the electrical conductors 18. The dielectric layer 20 cooperates with the spacer 24 to form the sides of the isolated flow paths 112-116. The dielectric layer 20 may be formed from a UV or heat-curable dielectric material that is screen printed onto the electrical conductors 18 and the electrode support substrate 16 during manufacture of the test sensor 100. An example of the material that forms the dielectric layer 20 may be the UV-curable material ELECTRODAG™ PF-455BC, as commercially available from Henkel Electronic Materials, Westerlo, Belgium. Another example of the material that forms the dielectric layer 20 may be the heat-curable INSULAYER™ series of materials available from Ecron Inc. Wareham, MA, USA. Other dielectric materials may be used to form the dielectric layer 20 that provide the desired insulation of the electrical conductors 18 from the sample and that are compatible with the analysis of the sample. The thickness (height) of the dielectric layer 20 is additive to that of the spacer 24 and may be chosen to provide the desired volume and sample capillary flow from the inlet 111 to the electrodes of the five isolated flow paths 112-116 in combination with the thickness of the spacer 24. For example, the thickness of the spacer 24 and dielectric layer 20 in combination may be from 102 micrometers (um) to 1,400 um. The spacer 24, the dielectric 20, and the cover 128 in combination provide a known cross-sectional area for each of the five isolated flow paths 112-116.

A first chemical reaction zone 170 provides the first chemical reaction zone through which the sample flows. The first chemical reaction zone 170 includes an immobilized lysing matrix residing on the electrode support substrate 16 at the general location of where the common flow inlet 110 is formed. The divided flow inlet 109 prevents the sample traveling within the divided flow inlet 109 from contacting the first chemical reaction zone 107. When a sample is applied to the inlet 111, the sample at least partially contacts the first chemical reaction zone 170 before reaching the common flow inlet 110 and dividing to flow into the isolated flow paths 113-116 for analysis at the electrodes. Preferably, the portion of the sample not following the divided flow inlet 109 contacts the first chemical reaction zone 170. Similarly, the portion of the sample following the divided flow inlet 109 to reach the isolated flow path 112 does not contact the first chemical reaction zone 170.

The immobilized lysing matrix includes a web or supporting viscous mass to immobilize a lysing agent.

The web of the immobilized lysing matrix may be a fibrous polymeric structure in a dried or semi-dried state. The web of the immobilized lysing matrix may be formed from woven polyester, such as the PES 18/13 matrix commercially available from SaatiTech Somers, NY 10589, having a Part No. 7-255-40, or from a PET 255-micron 40% open area woven matrix as available from Sefar, Hinterbissaustrasse 129410 Heiden, Switzerland.

The web of the immobilized lysing matrix may be replaced with a supporting viscous mass, including fumed silica, such as CABOSIL™, glass beads, glutaraldehyde, and other highly viscous polymeric materials that are non-chemically reactive with the constituents of the analysis, but that hold a lysing or other agent that would deactivate an active enzyme or proteolytic reagent.

The immobilized lysing matrix includes a lysing reagent sufficient to cause lysing of red blood cells in the sample before the electrochemical analysis. The immobilized lysing matrix lyses the red blood cells to release hemoglobin and other debris from the interiors of the red blood cells.

The lysing reagent may be applied to the web to form the immobilized lysing matrix by spray coating a first side ("top") of the web with the lysing reagent and drying the lysing reagent onto the first side of the web. Drying may occur from 30 to 45 degrees C. for from 1 to 30 minutes. Other methods of applying the lysing reagent to the web may be used. The lysing reagent may include a lysing agent, a buffer, and polymer adhesives, and thus may be formed by combining the lysing agent with the buffer and polymer or polymers. The lysing agent may be combined with the components of the buffer and polymer/s through physical mixing, such as with a magnetic stirrer, homogenizer, sonicator, and the like.

Suitable lysing agents for forming the lysing reagent include Saponin, cetyltrimethylammonium bromide (CTAB), tetradecyltrimethylammonium bromide (TTAB), Triton X-100, Tween agents (e.g., Tween 20), sodium dodecyl sulfate (SDS), polyoxyethylene lauryl ethers (POEs), Nonidet P-40 (NP-40), amphoteric surfactants, such as AMMONYX® Lo Special, Sodium Deoxycholate, Pancreatic Phospholipase, and the like. One or more lysing agents may be used in combination. Of these lysing agents, a mixture of Saponin, Triton X-100, and SDS is presently preferred.

The lysing agent concentration of CTAB in the lysing reagent may be from 2 to 15 millimolar (mM), preferably from 4 to 10 mM, and more preferably from 6 to 8 mM. The lysing agent concentration of SDS in the lysing reagent may be from 0.5 to 2 millimolar (mM), preferably from 0.8 to 1.6 mM, and more preferably from 1.1 to 1.3 mM. The lysing agent concentration of Sodium Deoxycholate in the lysing reagent may be from 3.5 to 14 millimolar (mM), preferably from 5 to 12 mM, and more preferably from 7 to 10 mM. The lysing agent concentration of AMMONYX® Lo Special in the lysing reagent may be from 0.05 to 0.2 millimolar (mM).

Depending on the selected lysing agent, suitable buffers may include sodium borate, tris(hydroxymethyl)aminomethane (Tris), 2-Amino-2-methyl-propan-1-ol (AMP), and N-Cyclohexyl-2-aminoethanesulfonic acid (CHES). When the lysing agent is Saponin, the CHES buffer, as available from Sigma-Aldrich, St. Louis, Mo., is presently preferred.

The first chemical reaction zone 170 also includes an interference reduction matrix that reduces lysate interference from lysed red blood cells, such as arising from glutathione and catalase interference. The interference reduction matrix preferably resides on a second side ("bottom") of the web. Thus, when the sample passes through the first chemical reaction zone 170, the sample first contacts the first side of the web and then contacts the second side of the web. In this manner, the first side of the web may lyse the red blood cells while the bottom of the web may reduce the interference that would otherwise arise from the constituents released from the lysed red blood cells during later stages of the analysis.

The interference reduction matrix includes one or more red blood cell (RBC) constituent interference reducers, such as sodium azide, Dess-Martin periodinane, N-ethyl maleimide, sodium iodoacetate, sodium periodate, and N-chloro 4-methylbenzenesulfonamide salt. Presently, sodium azide is the preferred interference reducer. The RBC interference reducer irreversibly chemically alters glutathione and catalase and renders them inert to downstream active enzyme, protein cleaving reagents, and the like.

The interference reduction matrix also includes one or more thickening agents, such as polyvinyl alcohol (PVA), hydroxyethylcellulose (e.g. NATROSOL™), poly(ethylene oxide) (PEO), and the like that prevents the one or more RBC interference reducers from entering the sample and flowing downstream. At present a weight ratio of approximately 1-2 (PVA): 0.5-1.5 (Natrasol): 0.5 (PEO) is preferred; however, other thickening agents in different ratios may be used depending on the constituents of the analysis.

The components used in the interference reduction matrix are chemically compatible with the RBC interference reducer and the analysis. Preferably, the interference reduction matrix irreversibly chemically alters and thus renders inert at least 70%, preferably at least 80%, and more preferably at least 90% of the otherwise downstream chemistry deactivating constituents released from the lysed red blood cells.

Second chemical reaction zones 175 and 176 provide the second chemical reaction zones through which divided portions of the sample flow. Thus, each of the isolated flow paths 112-116 may or may not include a second chemical reaction zone. In FIG. 1, the second chemical reaction zones 175 and 176 are provided in the isolated flow paths 115 and 116, respectively, while the isolated flow paths 112, 113, and 114 lack second chemical reaction zones. The second chemical reaction zones 175, 176 may slow the movement of the sample through the second chemical reaction zones 175, 176.

The second chemical reaction zones 175 and 176 include protein cleaving reagents. Thus, after the sample divides into the isolated flow paths 112-116, the sample contacts a first protein cleaving reagent forming the second chemical reaction zone 175 when flowing through the isolated flow path 115, and contacts a second protein cleaving reagent forming the second chemical reaction zone 176 when flowing through the isolated flow path 116. Preferably, during the analysis the second chemical reaction zones 175 and 176 are heated to a temperature from 55 to 75 degrees Celsius, preferably from 55 to 65 degrees Celsius.

The second chemical reaction zones 175, 176 include protein cleaving reagent sufficient to reduce the length of at least one peptide (amino acid) chain in the sample before the electrochemical analysis. Preferred proteolytic agents include DISPASE™ I (neutral protease, grade I), commercially available from Roche Diagnostics USA, Indianapolis, IN, proteinase K, and NEP-201 or NEP-801 Neutral Proteinase, commercially available from Toyobo, 2-8, Dojindo Hama 2-chome, Kita-ku, Osaka 530-8230 Japan, pepsin, renin, and papain. Of these proteolytic agents, NEP-201 Neutral Proteinase is presently preferred. For example, the proteolytic reagent may reduce the relatively long chain of Frutosyl Val-His-Leu-Thr-Pro to the relatively shorter chain of Fructosyl Val-His, as will be discussed further below. In the case of neutral proteolytic agents, the protein cleaving reagent is preferably buffered to 7.0 to 8.2 to enhance the activity of the proteolytic agent.

The second chemical reaction zones 175, 176 immobilize the desired proteolytic reagent. The desired proteolytic reagent may be immobilized at the second chemical reaction zones 175, 176 using a polymeric binder, or a polymeric binder in combination with a web or supporting viscous mass, as previously described.

The protein cleaving reagent may be mixed with the polymeric binder, or applied to a polymeric binder in combination with a web or supporting viscous mass by spray coating. Other methods of applying the protein cleaving reagent to the web may be used.

Polymeric binders include polyvinyl alcohol (PVA), polyvinylpyrrolidone (PVP), and other viscous polymeric materials that are compatible with the other constituents of the analysis and do not significantly adversely affect the active enzyme or enzymes at the electrical reaction zones 190. Unlike the thickening agents of the first chemical reaction zone 170, the polymeric binder of the second chemical reaction zone 175, 176 preferably includes a mixture of two polymers, with one polymer being more hydrophilic than the other.

Presently, a blend of PVA and PVP is preferred as the polymeric binders, with PVP being the more hydrophilic of the two. More preferred is a blend of PVA and PVP in an approximate 2:1 ratio by weight. Thus, while PVA may be used as a thickener in the first chemical reaction zone, if used in the second chemical reaction zone, it is combined with a more hydrophilic polymer. Other polymeric binders may be used depending on the reagents present in the first and/or second chemical reaction zones.

pH adjustment zones 180, through which a divided portion of the sample flows, preferably lie after the first and second chemical reaction zones, and are thus physically separated from the first and the second chemical reaction zones. The pH adjustment zones 180 reside between the first chemical reaction zone 180 and electrical reaction zones 190, and may or may not reside between any optional second chemical reaction zones and the electrical reaction zones 190. Thus, each of the isolated flow paths 112-116 may or may not include a pH adjustment zone. In FIG. 1, the pH adjustment zones 184, 185, and 186 are provided in the isolated flow paths 114, 115, and 116, respectively.

The pH adjustment zones 180 include at least one buffer, a polymeric binder, or a polymeric binder in combination with a web or supporting viscous mass, as previously described in the context of the second chemical reaction zones 175, 176. The at least one buffer is selected to provide the desired pH for the active enzyme at the electrical reaction zones 190. For example, if a pH of 6.8 is desired at the electrical reaction zones 190, a suitable buffer would be Chess. Other suitable buffers could be those as provided by Sigma-Aldrich that achieve the desired pH at the electrical reaction zones 190 while maintaining compatibility with the analysis and sample constituents.

The pH adjustment zones 180 alter the chemistry of the sample. By altering the pH of the sample, the pH adjustment zones 180 deactivate or substantially reduce the activity of a reagent in the sample released from the second chemical reaction zones. For the protein cleaving reagent of the second chemical reaction zones, the pH adjustment zones 180 may include a buffer that alters the pH from the high pH, such as greater than eight to nine, to a pH closer to neutral, such as from 6 to 7. Thus, the pH of the pH adjustment zones 180 may be approximately 6. The pH adjustment zones 180 may alter the sample pH to be compatible with the chemistry of the later electrical reaction zones 190, where enzymes such as Fructosyl amino oxidase (FAOX/FAOD) are present. Preferably the pH adjustment zones 180 reduce the activity of a proteolytic reagent by at least 30%, preferably by at least 70%. For example, a proteolytic reagent that is ~90% active at PH ~8 and is ~60% active at pH ~6, undergoes a greater than 30% reduction in activity at the lower pH of the pH adjustment zones 180.

The electrode support substrate 16 supports the electrical conductors 18. The electrode support substrate 16 may be formed from a wide variety of insulating materials that provide the desired stiffness to form a substrate for the electrical conductors 18. Suitable insulating materials include glass, ceramics, vinyl polymers, polyimides, polyesters, and styrenics. Preferably, flexible polymers form the electrode support substrate 16, with polyester and polyimide being more preferred. Preferred materials include MYLAR®, MELINEX ST 504®, and films with similar heat stabilization and adhesion, such as available from DuPont Tejjin Films, United States.

The electrical conductors 18 include isolated conductors that provide electrical conductivity to the electrodes of the test sensor 100. The test sensor 100 may include counter electrodes 120, reference electrodes 130, and working electrodes 140. As the test sensor 100 is represented with five isolated flow paths 112-116, the test sensor 100 includes five counter electrodes 122, 123, 124, 125, 126; five reference electrodes 132, 133, 134, 135, 136; and five working electrodes 142, 143, 144, 145, 146. In this way, each of the five isolated flow paths 112-116 includes a dedicated counter electrode, a dedicated reference electrode, and a dedicated working electrode. Each of the 15 electrodes is in electrical communication with a dedicated electrical conductor that provides independent electrical addressability to the electrode. In addition to providing electrical conductivity to the electrodes, one or more electrical conductors may be left bare and exposed to the sample.

The material forming the electrical conductors 18 is electrically conductive and may be gold, platinum, palladium, iridium, silver, or alloys of these metals, since such metals and their alloys are relatively unreactive, or can be made relative unreactive through a chemical process, when exposed to blood samples. Presently preferred materials for forming the electrical conductors 18 are gold and platinum. The electrical conductors may be screen-printed onto the electrode support substrate 16 or by laser ablation of a film on the electrode support substrate 16 of the electrically conductive material that will form the electrical conductors 18. Other ways of forming the electrical conductors 18 on the electrode support substrate 16 may be used.

Counter electrodes 120 are formed from a conductive material that provides a complete electrical circuit when paired with a working electrode. The conductive material may the same material that forms the electrical conductors 18, or a conductive material in electrical communication with the material forming the electrical conductors 18. The conductive material forming the counter electrodes 120 is preferably non-chemically reactive during the analysis of the sample and may or may not provide an independent potential in the presence of an applied potential.

Preferable conductive materials for forming the counter electrodes 120 include platinum, gold, rhodium, iridium, rhodium, ruthenium, silver, carbon, combinations of these metals with carbon, and a mixture of these metals with an ionic salt, such as AgCl. A more preferable conductive material for forming the counter electrodes 120, other than for counter electrode 123, is Ag/AgCl. A preferable conductive material for forming the counter electrode 123 is a material that does not provide an independent potential in the presence of an applied potential, such as carbon, platinum, gold, palladium, and mixtures thereof. A more preferred conductive material for forming the counter electrode 123 is carbon.

Counter electrodes 122-126 each may have an area from 1 $mm^2$ to 12 $mm^2$, preferably from 2 $mm^2$ to 8 $mm^2$, and more preferably from 2 $mm^2$ to 6 $mm^2$, which may be changed depending on the desired current carrying capacity for the test sensor 100 in relation to the chosen conductive material. The desired current carrying capacity for the test sensor 100 is from 5 to 100 micro amps (uA), with from 10 to 40 uA being preferred.

The conductive material for the counter electrodes 120 may be applied to the desired portion of the electrical conductors 18 through screen-printing. Other methods including lamination followed by laser ablation, laser scribing, mechanical scribing, or photolithography may be used. When the sample enters the test sensor 100 and branches into the isolated flow paths, the sample reaches the working electrodes 140 after crossing the counter electrodes 120 and the reference electrodes 130.

One or more counter electrode reagents may be deposited on the conductive material of each counter electrode to form a chemically active counter electrode. The counter electrode reagents may be applied to the desired portion of the conductive material forming the counter electrodes 120 through screen-printing. Other methods including ink-jetting, positive displacement deposition, spray coating, and the like may be used to apply the counter electrode reagents to form the counter electrodes 120.

The counter electrode reagent may be a redox counter electrode reagent deposited on the conductive material of the counter electrodes 120. The redox counter electrode reagent for the counter electrodes 120 assists in the transfer of electrons from the sample to the counter electrodes 120. Preferably, the counter electrode 123 includes a redox reagent as the redox counter electrode reagent.

Reference electrodes 130 are formed from a conductive material that provides a known independent potential when a potential is applied before, during, or after the analysis. The conductive material forming the reference electrodes 130 is preferably non-chemically reactive during the analysis of the sample. Preferable conductive materials for forming the reference electrodes 130 include Ag/AgCl and copper/copper sulfate (Cu/Cu(II)). A more preferable conductive material for forming the reference electrodes 130 is Ag/AgCl. Reference electrodes 132-136 each may have an area from about 0.2 $mm^2$ to about 0.6 $mm^2$, preferably from about 0.2 $mm^2$ to about 0.4 $mm^2$, which may be changed depending on the desired current carrying capacity for the test sensor 100 in relation to the chosen conductive material. The conductive material for the counter electrodes 130 may be applied to the desired portion of the electrical conductors 18 through screen-printing. Other methods including lamination followed by laser ablation, laser scribing, mechanical scribing, or photolithography may be used. When the sample enters the test sensor 100 and branches into the isolated flow paths, the sample crosses the reference electrodes 130 after crossing the counter electrodes 120.

Working electrodes 140 are formed from a conductive material that provides a complete electrical circuit when paired with a counter electrode. The conductive material may the same material that forms the electrical conductors 18, or a conductive material in electrical communication with the material forming the electrical conductors 18. The conductive material forming the working electrodes 140 is preferably non-chemically reactive during the analysis of the sample and preferably does not provide an independent potential when a potential is applied.

Preferable conductive materials for forming the working electrodes 140 include platinum, palladium, iridium, carbon, and combinations thereof. More preferable conductive materials for forming the working electrodes 140 include platinum, platinum/carbon combinations, palladium, and iridium. For working electrode 143, carbon is the preferred conductive material.

Working electrodes 142-146 each may have an area from 1 mm$^2$ to 12 mm$^2$, preferably from 2 mm$^2$ to 8 mm$^2$, and more preferably from 2 mm$^2$ to 6 mm$^2$, which may be changed depending on the desired current carrying capacity for the test sensor 100 in relation to the chosen conductive material. The conductive material for the working electrodes 140 may be applied to the desired portion of the electrical conductors 18 through screen-printing. Other methods including lamination followed by laser ablation, laser scribing, mechanical scribing, or photolithography may be used. When the sample enters the test sensor 100 and branches into the isolated flow paths, the sample crosses the counter electrodes 120 before reaching the working electrodes 140.

One or more working electrode reagents may be deposited on the conductive material of each working electrode to form a chemically active working electrode. The working electrode reagents may be applied to the desired portion of the conductive material forming the working electrodes 140 through screen-printing. Other methods including ink-jetting, positive displacement deposition, spray coating, and the like may be used to apply the working electrode reagents to form the working electrodes 140.

Working electrode 142 determines the hematocrit (Hct) content of the sample. The working electrode 142 is the selected working electrode conductive material without a working electrode reagent. The working electrode 142 and counter electrode 142 preferably provides no additional chemistry to the analysis. Thus, when electrically combined with the counter electrode 122, the working electrode 142 can perform electrochemistry on the sample to generate a Hct responsive output current. Thus, in addition to the timing values provided by the electrical conductors 151, 152, 154, and 156, applying a potential between electrical conductors 151$a$ and 158 energizes working electrode 142 and counter electrode 122, respectively to provide an output current that may be correlated with a reference correlation of known Hct sample contents. The current obtained from the Hct working and counter electrodes may be used alone or in combination with that obtained from one or more of the time values to determine the Hct content, sample viscosity, and the like, as discussed further below.

Working electrode 143 determines the total hemoglobin (THb) content of the sample. The working electrode 143 is the selected conductive material with a redox working electrode reagent deposited on the conductive material. The redox working electrode reagent for the working electrode 143 assists in the transfer of electrons from the sample to the electrodes. The same redox reagent may be used on the working electrode 143 and the counter electrodes 120, or a different redox reagent may be used on the working and counter electrodes. The redox reagent preferably is on both the working electrode 143 and on the counter electrode 123. Preferably, the redox reagent is ferricyanide. When electrically combined with the counter electrode 123, which may also include a redox counter electrode reagent deposited on the conductive material of the counter electrode 123, the working electrode 143 can perform electrochemistry on the sample to generate a THb responsive output current.

Working electrode 144 determines the endogenous HbA1c background of the sample. The working electrode 144 is the selected conductive material with an enzymatic working electrode reagent deposited on the conductive material. A preferred conductive material for the working electrode 144 is platinum. The enzymatic working electrode reagent for the working electrode 144 includes an enzyme on the conductive material that produces hydrogen peroxide from the HbA1c responsive by-products that would be produced in the second chemical reaction zone if the isolated flow path 114 included a second chemical reaction zone-which it does not. Thus, when electrically combined with the counter electrode 124, which also may have the enzymatic reagent on the conductive material, the working electrode 144 can perform electrochemistry on the sample to generate an output current responsive to any endogenous species that would generate a current that would be considered responsive to the HbA1c concentration of the sample, but that does not originate from the HbA1c held within the red blood cells of the blood sample.

Working electrode 145 determines the electrochemical background of the sample. The working electrode 145 is the selected conductive material without a working electrode reagent, thus having a similar construction to the working electrode 142. The working electrode 145 provides no additional chemistry to the analysis. Thus, when electrically combined with the counter electrode 125, the working electrode 145 performs electrochemistry on the blood sample that has been lysed in the first chemical reaction zone and cleaved in the second chemical reaction zone to generate an output current responsive to the sample without an HbA1c specific current component originating from the enzymatic working electrode reagent.

Working electrode 146 determines the HbA1c concentration of the sample. The glycated hemoglobin working electrode 146 is the selected conductive material with an enzymatic working electrode reagent deposited on the conductive material. A preferred conductive material for the working electrode 146 is platinum. As for the working electrode 144, the enzymatic working electrode reagent for the working electrode 146 includes an enzyme that produces hydrogen peroxide from HbA1c responsive by-products produced in the second chemical reaction zone. Thus, when electrically combined with the counter electrode 126, which may also have the enzymatic reagent on the conductive material, the working electrode 146 can perform electrochemistry on the sample to generate an output current responsive to the HbA1c concentration of the sample. The current from this electrode will include a substantive component that is responsive to the HbA1c concentration of the sample, but also will include components responsive to the endogenous HbA1c and electrochemical backgrounds of the sample.

After crossing the working electrodes 140, the sample may contact one or more distal electrical conductors positioned generally below the vents 29. These conductors are represented in FIG. 1, but unlabeled to increase clarity of the labeled structures. When the blood sample crosses the working electrodes 140 and reaches the distal electrical conductors the presence of the sample may be detected by applying a relatively low voltages, such as 100 millivolts (mV) across a working electrode and the associated distal electrical conductor. By contacting a working electrode and the respective distal electrical conductor, the sample completes an electrical circuit and the applied potential provides a current that may be detected and/or determined. A higher potential, such as 500 mV, applied across the working and counter electrodes may be used to analyze the sample Each of the isolated flow paths includes an electrical reaction zone 190. The electrical reaction zones 190 may include a working electrode reagent if one or more of the electrodes are coated with a reagent that alters the electrochemistry that would occur if a non-chemically active "bare" conductive material was used. Similarly, one or more of the reaction zones 190 may include a counter electrode reagent. Each electrical reaction zone is defined at least by a working electrode and a counter electrode; however, additional electrodes, such as a reference electrode, may be included in an electrical reaction zone. The electrical reaction zones 190 formed in the isolated flow paths are defined by the electrical conductors exposed to the sample in the individual isolated flow paths. Thus, after being divided, crossing the first chemical reaction zone 170, being divided again, and optionally crossing a second chemical reaction zone, the sample enters the electrical reaction zone 192-196 of each isolated flow path 112-116, respectively. Preferably, during the analysis the electrical reaction zones 190 are heated to a temperature from 35 to 54 degrees Celsius, preferably from 42 to 52 degrees Celsius.

Hct electrical reaction zone 192 is within the isolated flow path 112 and is defined by electrical conductor 158, which energizes counter electrode 122, and electrical conductor 151a, which energizes working electrode 142. Optional reference electrode 132 also is present. Counter electrode 122 and working electrode 142 lack reagents. In fact, the counter electrode 122 is optional, as the bare electrical conductor 158 may reside in the isolated flow path 112. Knowing the Hct content of the sample allows a more accurate HbA1c determination from the test sensor 100 when a disease state exists. Knowledge of Hct content allows for the HbA1c analysis to be corrected in the event the undiluted blood sample is drawn from an individual having sickle cell anemia, other forms of anemia, and the like, which result in an alteration in the flow rate of the blood. Without this information, two undiluted blood samples having identical HbA1c concentrations, but one with normal RBC and the other with abnormal RBC, may be determined to have different HbA1c concentrations by the measurement device.

Prior to reaching the electrical reaction zone 192 within the isolated flow path 112, the initially divided sample sequentially crosses electrical conductors 151, 152, 154, and 156. These conductors are present in the isolated flow path 112, which is the flow path that determines sample presence, in addition to determining the viscosity and hematocrit (Hct) content of the sample. When the sample crosses electrical conductors 151 and 152, an electrical circuit completes between these conductors, so a measurement device can determine that a sample was introduced to the test sensor 100. This current also provides a time one (T1) value for the analysis. When the sample then contacts electrical conductor 154, an electrical circuit completes with the electrical conductor 151, and the measurement device can determine a time two (T2) value for the analysis. When the sample then contacts electrical conductor 156 and the counter electrode 122 in electrical communication with the electrical conductor 158, the measurement device can determine a time three (T3) value for the analysis. As the cross-section of the isolated flow path 112 is known, the T1, T2, and T3 time values may be used to determine the viscosity of the sample. One or more of these time values may be compared to a reference correlation of these time values to determine sample Hct content, sample viscosity, and/or other physical properties of the sample. Preferably the timing values are used to determine sample viscosity and the Hct working and counter electrodes are used to determine sample hematocrit content.

THb electrical reaction zone 183 is within the isolated flow path 113 and is defined by electrical conductor 158, which energizes counter electrode 123, and electrical conductor 153, which energizes working electrode 143. Optional reference electrode 133 also may be present. The redox species at the working electrode 143 is reduced by the hemoglobin in the sample when a potential is applied across electrical conductors 158 and 153. The redox species at the counter electrode 123 also is reduced during the analysis as electrons flow from the working electrode to the counter electrode. If electrode polarity were reversed, so would electron flow. Knowing the THb concentration of the sample allows a more accurate HbA1c determination from the test sensor 100.

HbA1c Channel 1 electrical reaction zone 196 is within the isolated flow path 116 and is defined by electrical conductor 158, which energizes counter electrode 126, and electrical conductor 159, which energizes working electrode 146. Optional reference electrode 136 also is present. Counter electrode 126 lacks reagents, but working electrode 146 includes the analyte responsive enzyme reagent. The working electrode 146 provides an analyte responsive output current so a lysed and cleaved sample current in the presence of the analyte specific enzyme may be obtained.

For HbA1c analysis, a specific enzyme that produces hydrogen peroxide from a Fructosyl Val-His protein fragment is Fructosyl Amino Oxidase (FAOX/FAOD); however, other enzymes that produce hydrogen peroxide from the desired HbA1c responsive protein fragments may be used. Thus, the chemical reaction occurring at the working electrode 146 electrode may be represented as: Fructosyl Val-His+FAOX/FAOD=$H_2O_2$.

In the presence of the potential applied between the working electrode 146 and the counter electrode 126, the hydrogen peroxide releases electrons which provides an output current between the working and counter electrodes responsive to the rate and amount of hydrogen peroxide being converted. This reaction of $H_2O_2$ conversion may be represented as: $H_2O_2 \rightarrow O_2 + 2H^+ + 2e-$.

When the working electrode 146 includes a platinum component in the conductive material, such as platinum or a platinum/carbon combination, the electrochemical conversion of the hydrogen peroxide produces an output current that may be quantified and converted to grams/dL of HbA1c in the blood sample by the measurement device. However, while the output current obtained from the electrical reaction zone 196 is responsive to the HbA1c concentration of the sample as determined from the analysis, the current also is inclusive of the background currents obtained from the electrical reaction zones 194 and 195. Thus, the electrical reaction zone 196 generates an output current responsive to the HbA1c concentration of the sample, but also includes output current attributable to background that is preferably removed to determine the HbA1c concentration of the blood sample.

Electrochemical background Channel 2 electrical reaction zone 195 is within the isolated flow path 115 and is defined by electrical conductor 158, which energizes counter electrode 125, and electrical conductor 157, which energizes working electrode 145. Optional reference electrode 135 also is present. The working electrode 145 provides an electrochemical background responsive current so an output current from a lysed and cleaved sample may be obtained that does not include an enzyme reagent responsive output current component. Lacking the enzyme reagent responsive output current component, the output current from the electrical reaction zone 195 also lacks a HbA1c responsive current component. By omitting the analyte specific enzyme from the working electrode 145, an electrochemical background responsive output current may be determined that should be at least partially removed from the output current determined from the electrical reaction zone 196.

Endogenous background HbA1c Channel 3 electrical reaction zone 194 is within the isolated flow path 114 and is defined by electrical conductor158, which energizes counter electrode 124, and electrical conductor 155, which energizes working electrode 144. Optional reference electrode 134 also may be present. Counter electrode 124 lacks reagents, but working electrode 144 includes the analyte responsive enzyme reagent. The working electrode 144 provides an output current from a lysed, but un-cleaved sample in the presence of the analyte specific enzyme. Thus, the electrical reaction zone 194 provides an output current responsive to components of the blood sample that react with the enzyme of the enzymatic reagent to generate hydrogen peroxide not responsive to the HbA1c concentration. Hydrogen peroxide generated by the enzymatic reagent from the sample that is not responsive to the HbA1c concentration of the sample provides a non-analyte responsive output current component that should be at least partially removed from the output current determined from the electrical reaction zone 196.

The electrode support substrate 16 resides on a heater 160 that includes electrical heater conductors 162, heating elements 164, and a resistive layer 168. The heater 160 residing on base 14 provides heat to one or more of the chemical and electrical reaction zones. The heater 160 may provide one temperature or multiple temperatures to different portions of the test sensor 100. The electrical heater conductors 162 are configured to provide electrical communication between the heating elements 164 and the measurement device. The substrate 16 resides on the resistive layer 168, which resides on the heating elements 164.

The electrical heater conductors 162 are formed from a conductive material such as silver, gold, copper, and the like. The heating elements 164 may be formed from the same material as the electrical heater conductors 162 or from an alternative conductive material. Preferably, the electrical heater conductors 162 and the heating elements 164 are formed from the same conductive material, with a preferable conductive material being silver.

The conductive material for the heater 160 may be applied to the desired portion of the base 14 through screen-printing. Other methods including lamination followed by laser ablation, laser scribing, mechanical scribing, or photolithography may be used to form the electrical heater conductors 162 and the heating elements 164.

The resistive layer 168 is formed from a mixture of conductive and non-conductive materials selected to provide the desired resistivity to the layer 168. Screen-printing may be used to deposit the resistive layer 168 on the heating elements 164.

Applying an electrical potential to electrical heater conductors 162 of the heater 160 causes the heating elements 164 to warm in response to the applied potential. In this way the heater 160 may warm the sample when chemical or electrochemical reaction is occurring.

The heater 160 resides on the base 14. The base 14 provides the test sensor 100 with a bottom. The base 14 may be formed from a polymeric material that has suitable flexibility for the manufacturing process. The base 14 is preferably an insulating plastic with an adhesive on one side. An example of such insulating plastic is ARCARE™7815, as available from Adhesive Research, York, Pa. As the base 14 does not contact the sample, more variability in the polymeric material selected for the base 14 is allowed.

Figure 2:
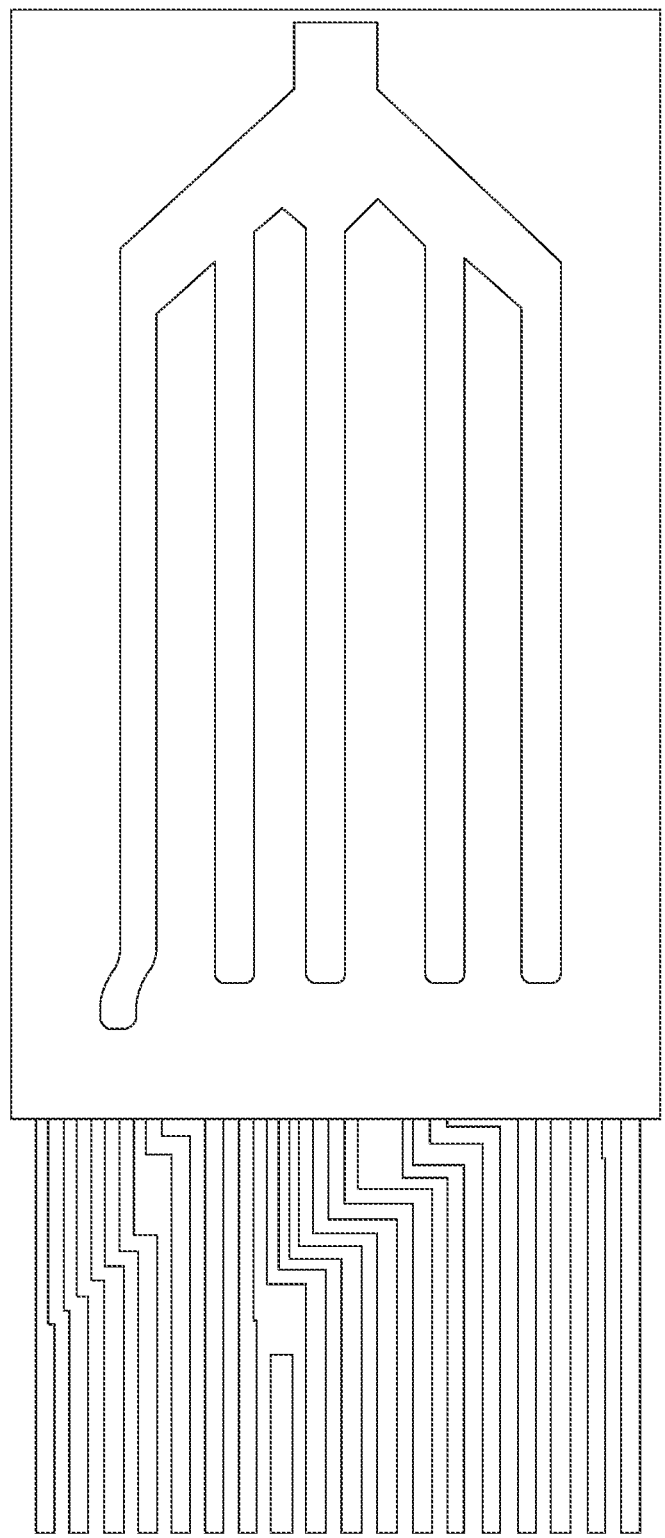
FIG. 2 represents the electrical connections for the test sensor.

FIG. 2 represents the electrical connections for the test sensor 100. When a potential is applied between any two electrical conductors, different electrodes or bare conductors may be energized.

Figure 3:
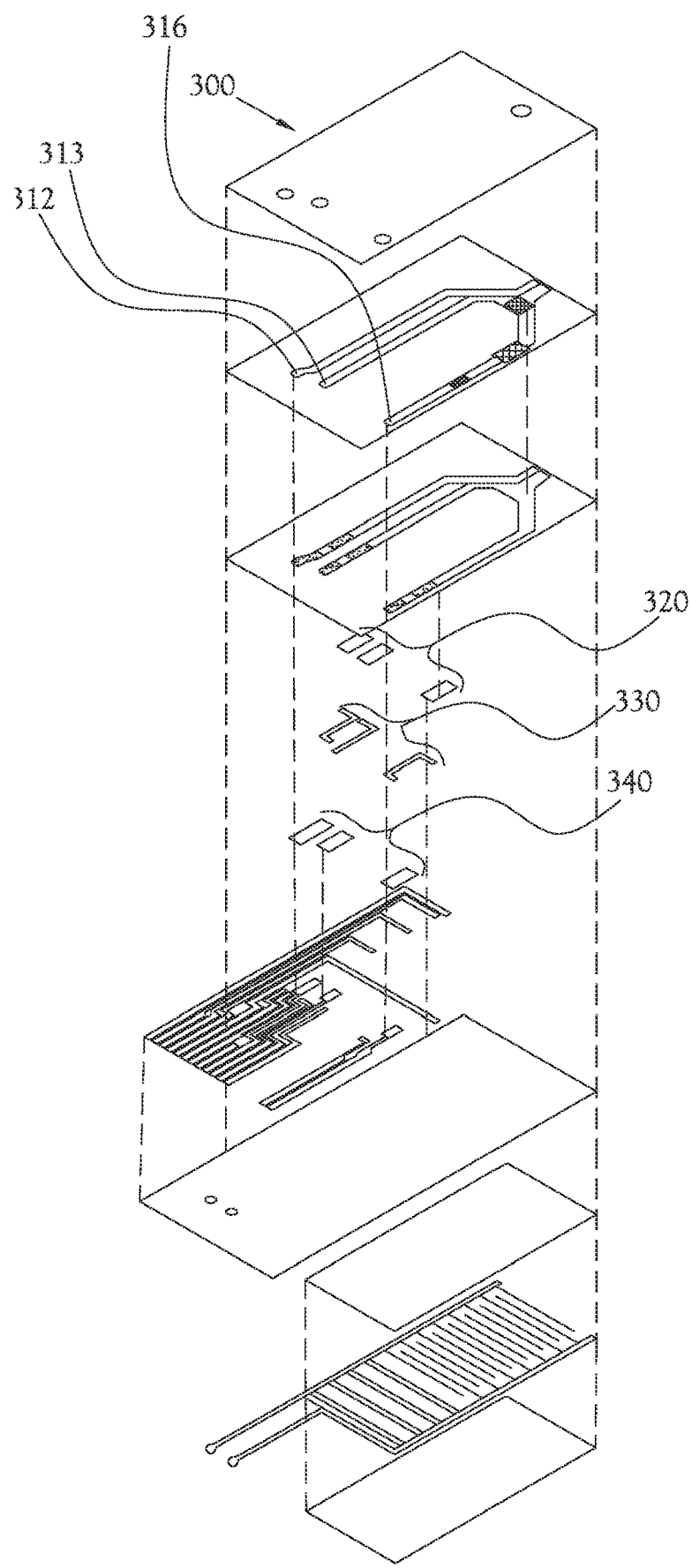
FIG. 3 represents a three-analysis-path test sensor.

FIG. 3 represents a three-analysis-path test sensor 300. In relation to the test sensor 100 of FIG. 1, the test sensor 300 of FIG. 3 eliminates the two isolated flow paths 114, 115 of FIG. 1 that provide background responsive output currents to the analyte analysis performed with test sensor 100. Thus, if the enhanced accuracy and/or precision provided by the additional background analysis paths of test sensor 100 are not needed, the test sensor 300 may be used.

The test sensor 300 includes a Hct analysis path 312, a THb analysis path 313, and an HbA1c analysis path 316. Thus, the test sensor 300 may provide an analysis of HbA1c in blood, but not to the level of accuracy or performance as provided by the test sensor 100 of FIG. 1 due to the elimination of the two HbA1c background paths that are responsive to background. A four-analysis-path test sensor (not shown) also could be constructed by eliminating one of the isolated flow paths, such as the endogenous HbA1c analysis.

Figure 4A:
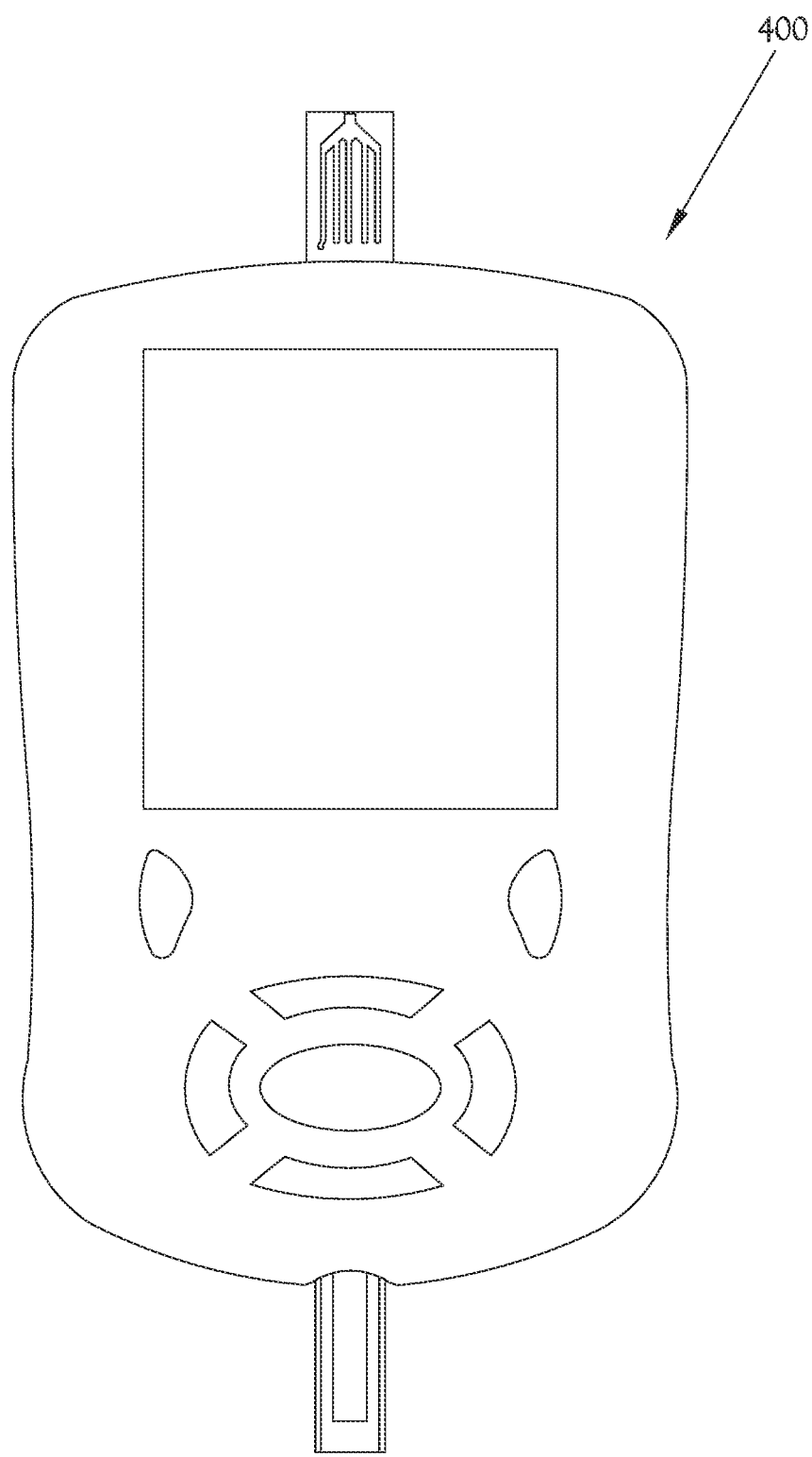
FIG. 4A represents an electrical measurement device that may be used to perform an analysis of the analyte in combination with the three or five analysis path test sensors.

FIG. 4A represents an electrical measurement device 400 that may be used to perform an analysis of the analyte in combination with the test sensors 100 or 300. The measurement device 400 includes electrical conductor contacts that electrically connect with the electrical conductors of the test sensor, and thus the electrodes of the test sensor. The electrical conductor contacts allow positioning of the test sensor for analysis of the blood sample and for removal of the test sensor from the measurement device 400 when the analysis is complete. The sample completes the electric circuit when the sample is applied to the electrodes. The measurement device 400 may be activated manually, such as with a button, by the insertion of the test sensor, or by the sample completing a circuit within the test sensor. For example, a relatively low potential of 100 mV may be applied between one or more working electrodes and the respective distal electrical conductors to determine that the test sensor is filled when a current of sufficient amperage is detected.

The measurement device 400 also applies and detects continuity between various electrical conductors to determine the rate at which the sample moves through an isolated flow path. The measurement device may have the processing capability to measure and correlate the electrical output measured from the multiple conductors of the test sensor with the presence and/or concentration of one or more analytes in the blood sample. The measurement device 400 also includes electrical heater contacts that connect with the electrical heater conductors of the test sensor to apply the potential to the heating elements that heats the sample during the analysis.

The measurement device 400 measures the electrical output from the test sensor as a current, as generated by amperometry. Amperometry is an electrochemical sample analysis where current is measured at a substantially constant potential (voltage) as a function of time as a substantially constant potential is applied across a working and counter electrode pair of the test sensor. The measured output current, which generally reaches an initial peak and then decays downward, is used to quantify the analyte in the sample contacting the working and counter electrode pair. Amperometry measures the rate at which an electrochemically active species is being oxidized or reduced near the working electrode. Many variations of the amperometric method for biosensors have been described. The measurement device 400 may be configured to apply a constant voltage from 200 mV to 650 mV between any working and counter electrode pair of the test sensor.

Additionally, the measurement device 400 is configured to apply a constant voltage from 3 to 14 volts across the electrical heater conductors of the test sensor. The measurement device 400 may apply a voltage to the heater conductors in response to the push of a button, by the insertion of the test sensor, or by the sample completing a circuit within the test sensor. Preferably, the measurement device 400 applies a voltage to the heater conductors in response to the insertion of the test sensor.

Figure 4B:
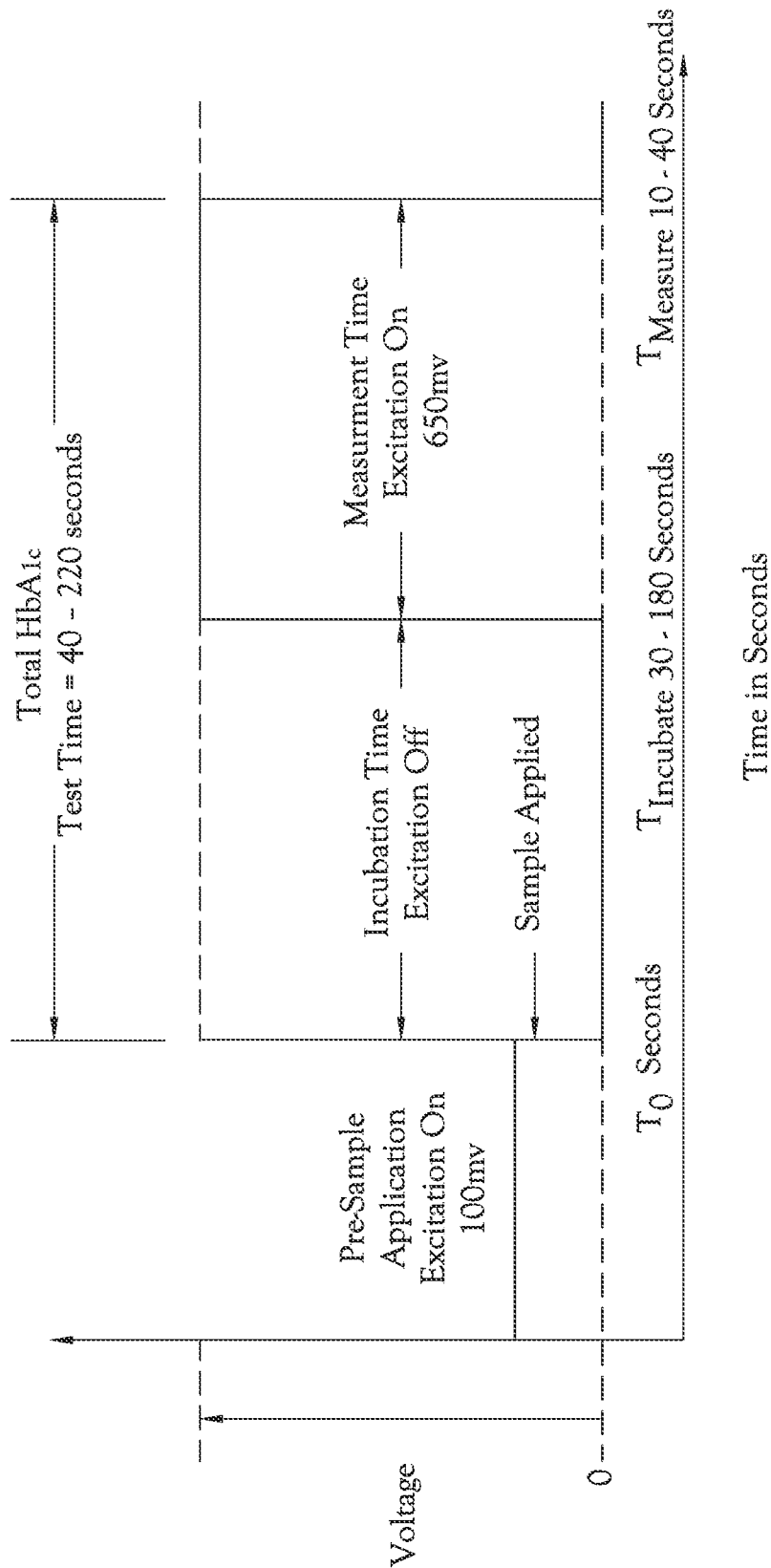
FIG. 4B represents a potential sequence that the measurement device may apply to one or more electrical reaction zones of a test sensor.

FIG. 4B represents a potential sequence that the measurement device 400 may apply to one or more of the electrical reaction zones 190. In this representative sequence, a potential of 100 mV is applied across a working and counter electrode pair, is turned off or substantially reduced during an incubation time, and then turned back on at a potential of 650 mV during a sample excitation time. The incubation time may be from 30 to 180 seconds and the sample excitation time may be from 10 to 40 seconds. Other voltages and times may be used depending on the specifics of the analysis.

The measurement device 400 is configured to provide a determination of mg/dL of HbA1c in the blood sample by measuring a current from a THb electrical reaction zone (such as 193 of the test sensor 100 in FIG. 1) and an HbA1c electrical reaction zone (such as 196 the of test sensor 100 in FIG. 1). The concentration of THb in the sample is determined from the measured current by measuring one or more output current values from the electrodes of a THb electrical reaction zone at one or more times during the analysis of the sample and comparing the measured value or values with a THb reference correlation. The concentration of HbA1c in the sample is determined from the measured current by measuring one or more output current values from the electrodes of a HbA1c electrical reaction zone at one or more times during the analysis of the sample and comparing the measured value or values with a HbA1c reference correlation. Then the measurement device 400 divides the grams of HbA1c by the grams of THb and multiplies by 100 to determine the percent HbA1c in the sample. Other mathematical techniques of determining the percent HbA1c in the sample from the measured HbA1c and THb output current values may be used.

The measurement device 400 corrects the determined HbA1c concentration of the sample or the output currents arising from the THb and HbA1c electrical reaction zones with information determined from the Hct isolated flow path. The output currents from the Hct isolated flow path or derivative timing values may be used to select the reference correlation used to determine the HbA1c concentration of the sample, may be used with a reference correlation to determine a correction value for the determined HbA1c concentration or determined percent PhB1c concentration, and the like. In this way, the final determined percent HbA1c concentration of the blood sample is corrected for the Hct content and abnormality of the sample.

The measurement device 400 optionally corrects the determined HbA1c concentration of the sample or the output currents arising from the THb and HbA1c electrical reaction zones with information determined from optional correction isolated flow channels, such as for electrochemical background, endogenous HbA1c, and the like. The output currents from these correction channels may be used to select the reference correlation used to determine the HbA1c concentration of the sample, be used with a reference correlation to determine a correction value for the determined HbA1c concentration, and the like. In this way, the final determined HbA1c concentration of the blood sample is corrected for electrochemical background, endogenous HbA1c, and the like.

Figure 5:
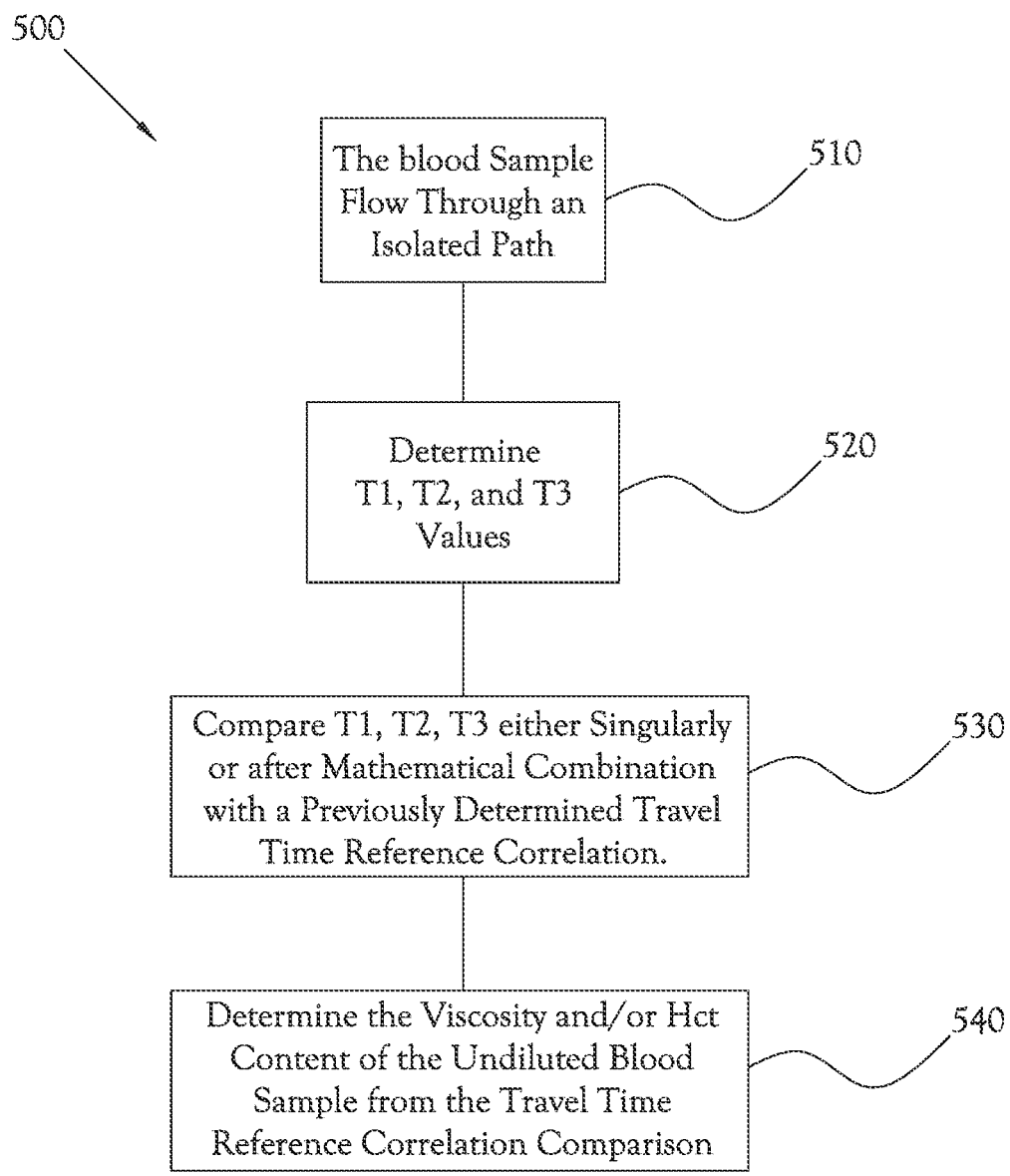
FIG. 5 represents a method of determining the viscosity of an undiluted blood sample that may be performed by the measurement device.

FIG. 5 represents a method 500 of determining the viscosity of an undiluted blood sample that may be performed by the measurement device 400 of FIG. 4A. The viscosity and Hct content of an undiluted blood sample are correlated. As the Hct content of the sample increases, so will the viscosity, and so will the travel time through an isolated flow path at the same temperature.

In 510, the blood sample flows through an isolated flow path (such as 112 of the test sensor 100 in FIG. 1) and sequentially crosses multiple pairs of conductors, such as 151/152, 151/154, and 156/158 of test sensor 100 of FIG. 1. In 520, the measurement device determines T1, T2, and T3 values, as previously described for circuit completion between each electrode pair. In 530, the measurement device 400 compares the T1, T2, and T3 values either singularly or after mathematical combination with a previously determined travel time reference correlation. The travel time reference correlation relates the previously determined T1, T2, and T3 values of blood samples of known viscosity and/or Hct content at a known temperature to the measured T1, T2, and T3 values of the sample either singularly or after mathematical combination. In 540, the measurement device 400 determines a viscosity and/or Hct content for the undiluted blood sample from the travel time reference correlation comparison.

Figure 6:
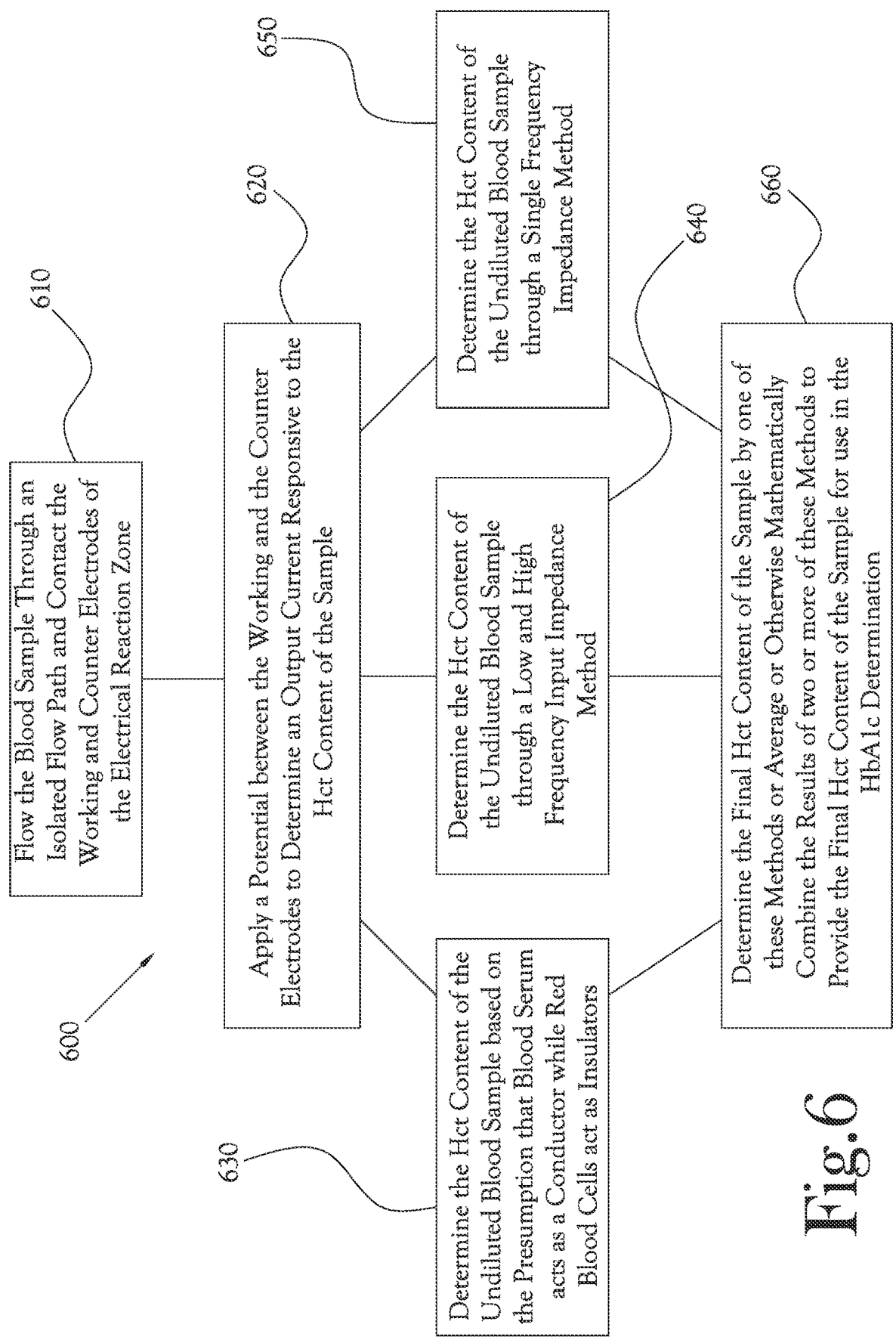
FIG. 6 represents a method of determining the Hct content of an undiluted blood sample that may be performed by the measurement device.

FIG. 6 represents a method 600 of determining the Hct content of an undiluted blood sample that may be performed by the measurement device 400 of FIG. 4A. In 610, the blood sample flows through an isolated flow path (such as 112 of the test sensor 100 in FIG. 1) and contacts the working and counter electrodes of the electrical reaction zone 192. In 820, the measurement device applies a potential between the working and the counter electrodes to determine an output current responsive to the Hct content of the sample. From the measured output current, the Hct content of the sample may be determined by at least one of three ways.

In 630, the Hct content of the undiluted blood sample may be determined based on the presumption that blood serum acts as a conductor while red blood cells act as insulators. Thus, the output current measured in response to the input potential is inversely proportional to the Hct content of the sample. The more current that flows, the fewer red blood cells are in the sample. A predetermined relationship between output currents and known Hct blood sample concentrations may be stored in the measurement device and used to determine the Hct content of a test sample. Additional discussion regarding this method of Hct determination may be found in U.S. Pat. No. 4,303,887.

In 640, the Hct content of the undiluted blood sample may be determined through a low and high frequency input impedance method. The resistance and reactance of the blood within the electrical reaction zone (a constant volume) may be measured at a low (50 kHz) and high (1 MHz) frequency. These duel frequency impedance measurements may then be used by the measurement device to determine the intracellular and extracellular (plasma) fluid volume of the undiluted blood sample, and thus the hematocrit content of the sample. Additional discussion regarding this method of Hct determination may be found in "An electronic method for Rapid measurement of hematocrit in blood samples", K Cha, RG Faris, EF Brown and DW Wilmore, Physiological Measurement, Volume 15, Number 2 May 1994.

In 650, the Hct content of the undiluted blood sample may be determined through a single frequency impedance method. The resistance or conductivity of the blood sample is determined at a fixed input frequency. For example, a square wave input of 30 to 50 Hz, preferably about 41 Hz may be used. The change in the resistance or conductivity of the sample is then measured as a function of frequency. A measurement of voltage, resistance, conductivity, and the like may be determined at a specific time and correlated with known values in a look-up table to determine the measured Hct content of the sample. Additional discussion regarding this method of Hct determination may be found in Comparative Analysis of Hematocrit Measurements by Dielectric and Impedance Techniques, Ernasto F. Treo et al., African Journal of Biotechnology, Vol. 9 (54), pp. 9295-9306, 27, December 2010.

In 660, the final Hct content of the sample is determined by one of these methods or the results of two or more of these methods may be averaged or otherwise mathematically combined to provide the final Hct content of the sample for use in the HbA1c determination. Additionally, as hemoglobin makes up approximately 30% of the Hct content of an undiluted blood sample unless a disease state exists, the determined final Hct content of the sample may be used as a check on the THb concentration of the sample determined by the measurement device, as described further below.

Figure 7:
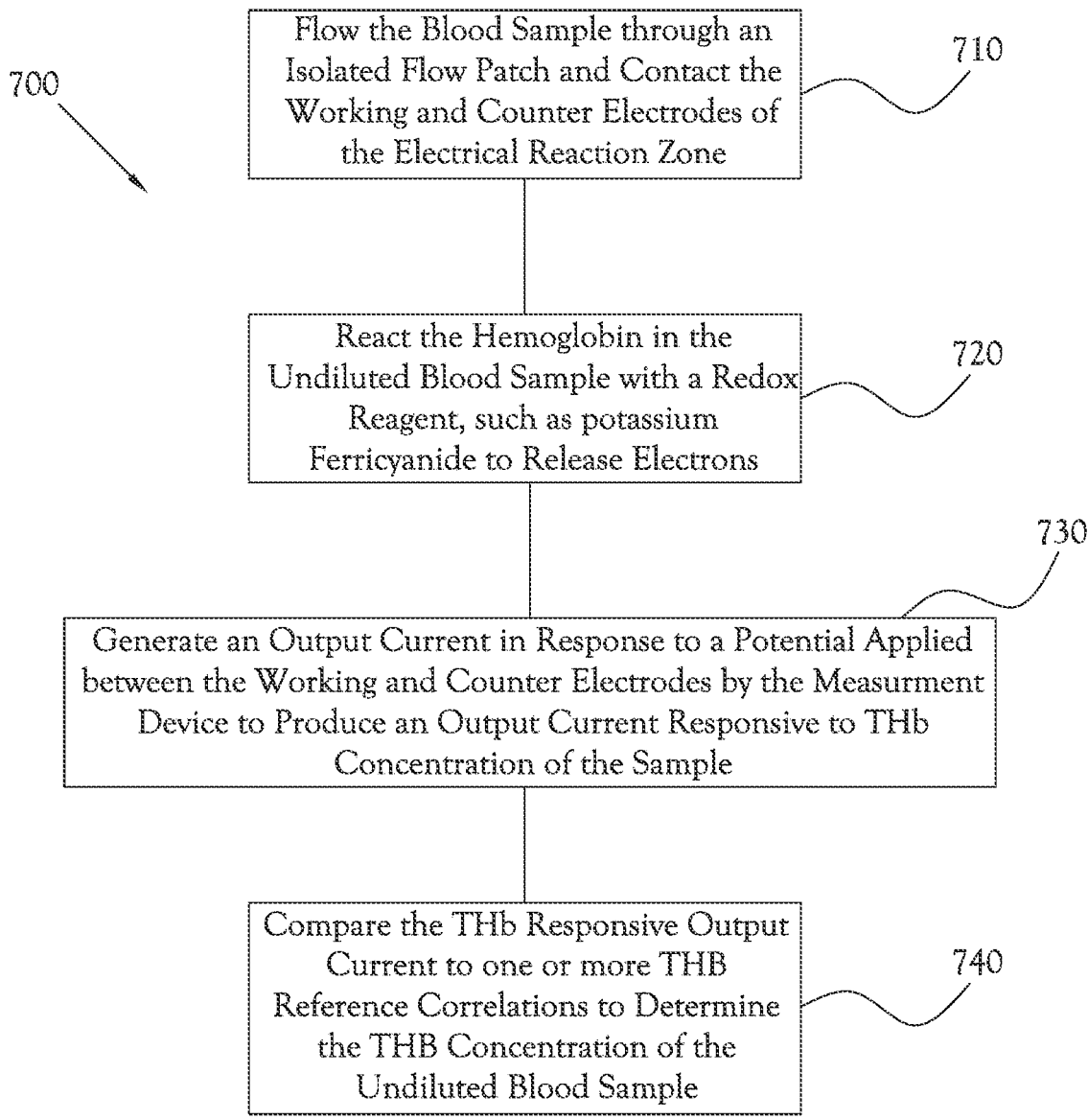
FIG. 7 represents a method of determining the THb concentration of an undiluted blood sample that may be performed by the measurement device.

FIG. 7 represents a method 700 of determining the THb concentration of an undiluted blood sample that may be performed by the measurement device 400 of FIG. 4A. In 710, the blood sample flows through an isolated flow path (such as 113 of the test sensor 100 in FIG. 1) and contacts the working and counter electrodes of the electrical reaction zone 193. In 720, the hemoglobin in the undiluted blood sample reacts with a redox reagent, such as potassium ferricyanide to release electrons. In 730, the released electrons generate an output current in response to a potential applied between the working and counter electrodes by the measurement device to produce an output current responsive to the THb concentration of the sample. In 740, this THb responsive output current measured at one or more times during the analysis may be compared to one or more THb reference correlations to determine the THb concentration of the undiluted blood sample.

Figure 8A:
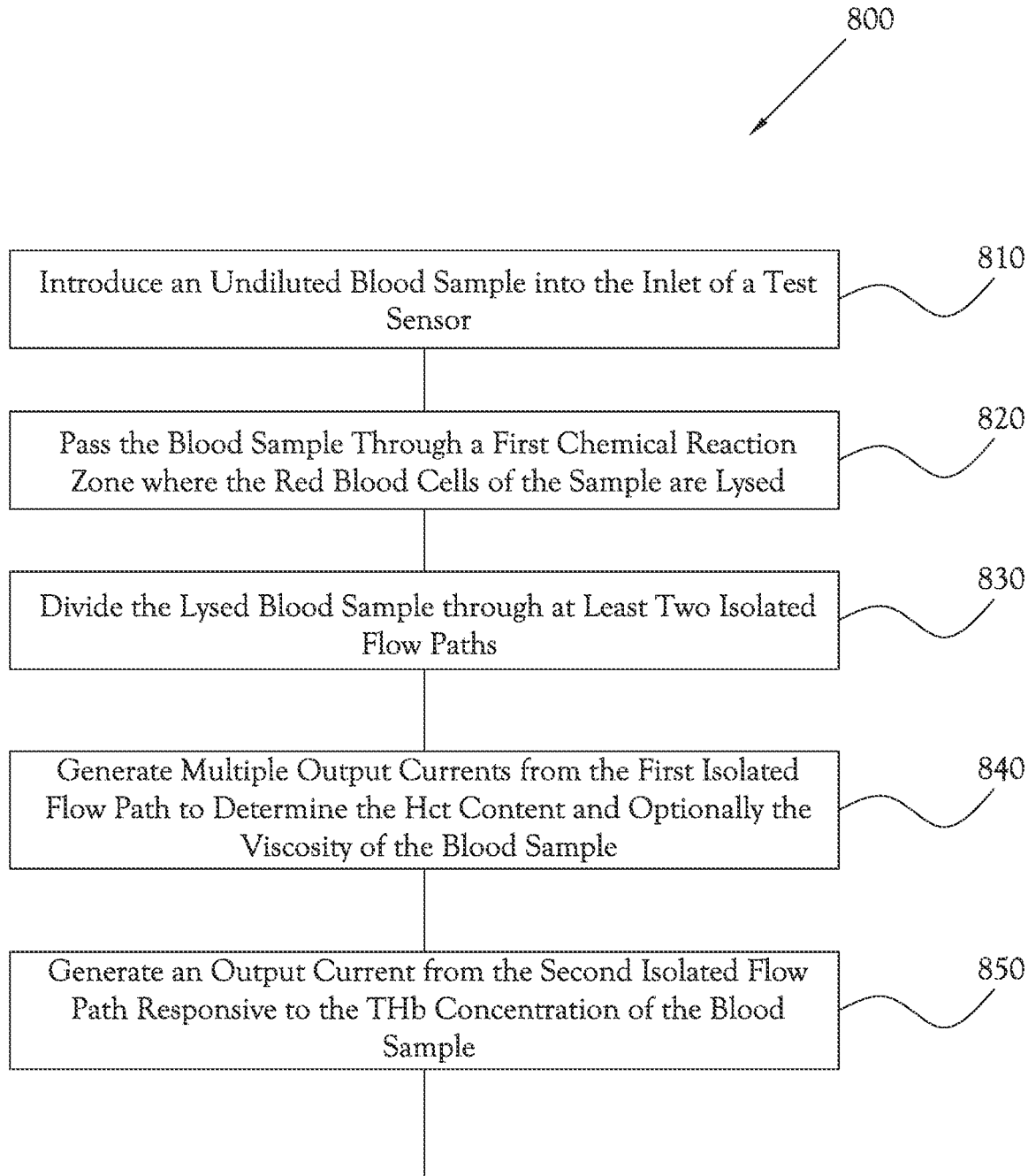
FIGS. 8A & 8B represent a method of electrochemically determining the HbA1c content of an undiluted blood sample with at least two channels of correction that may be performed by the measurement device.
Figure 8B:
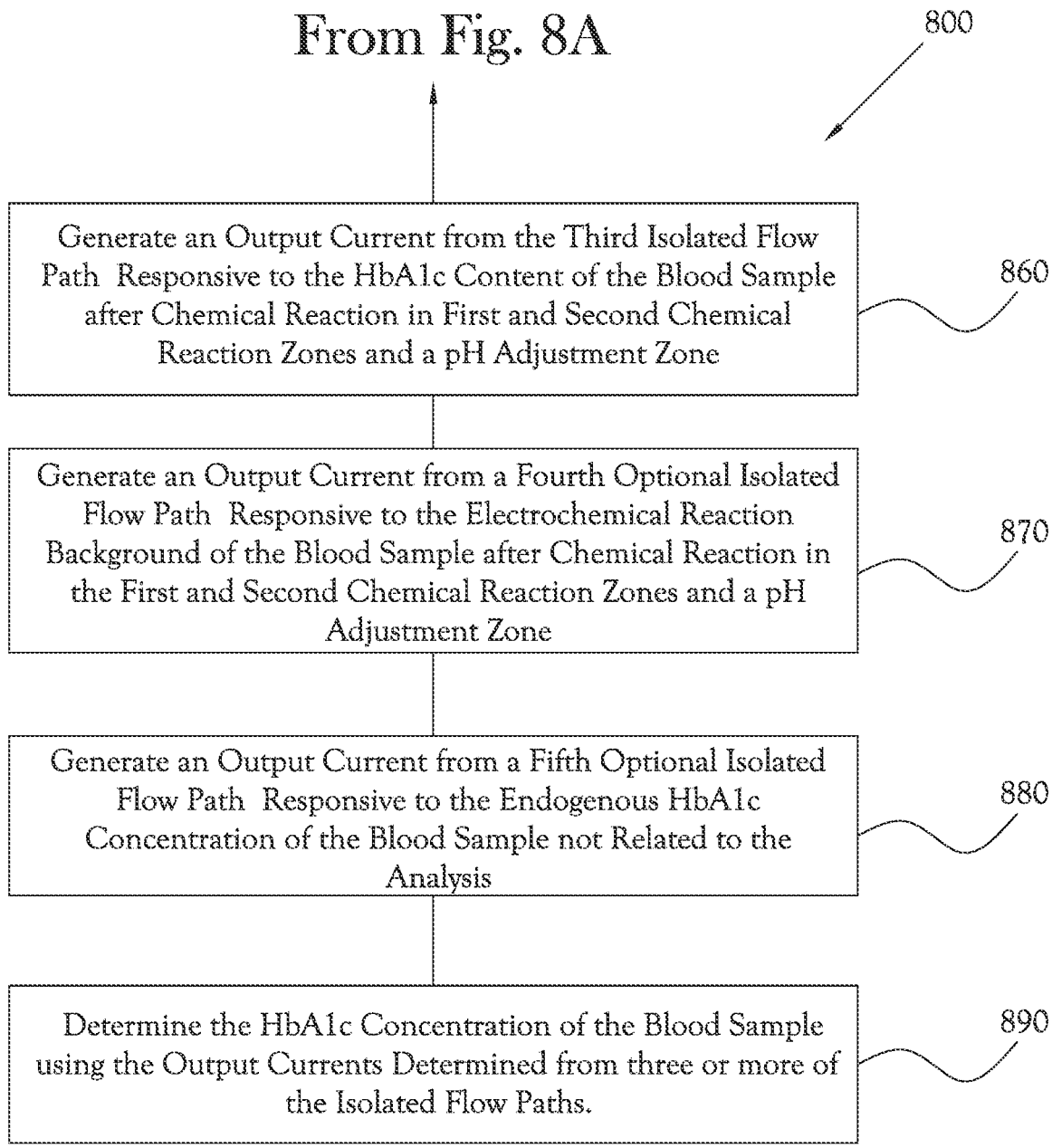

FIG. 8 represents a method 800 of electrochemically determining the HbA1c content of an undiluted blood sample with at least two channels of correction that may be performed by the measurement device 400 of FIG. 4A. In 810, an undiluted blood sample, such as taken from a vein or artery, is introduced to the inlet of a test sensor, such as the test sensor 100 of FIG. 1. In 820, the blood sample passes through a first chemical reaction zone where the red blood cells of the sample are lysed. In 830, the lysed blood sample is divided so it flows through at least two isolated flow paths. In the first un-lysed flow path 840, multiple output currents are generated allowing determination of the Hct content and optionally the viscosity of the blood sample. In second flow path 850, an output current is generated that is responsive to the THb concentration of the blood sample. In third flow path 860, an output current is generated that is responsive to the HbA1c content of the blood sample after chemical reaction in first and second chemical reaction zones and pH adjustment. In a fourth optional flow path 870, an output current is generated that is responsive to the electrochemical background of the blood sample after chemical reaction in the first and second chemical reaction zones and pH adjustment. In a fifth optional flow path 880, an output current is generated that is responsive to the endogenous HbA1c concentration of the sample not related to the analysis. In 890, the measurement device determines the HbA1c concentration of the blood sample using the output currents determined from three or more of the isolated flow paths.

Figure 9:
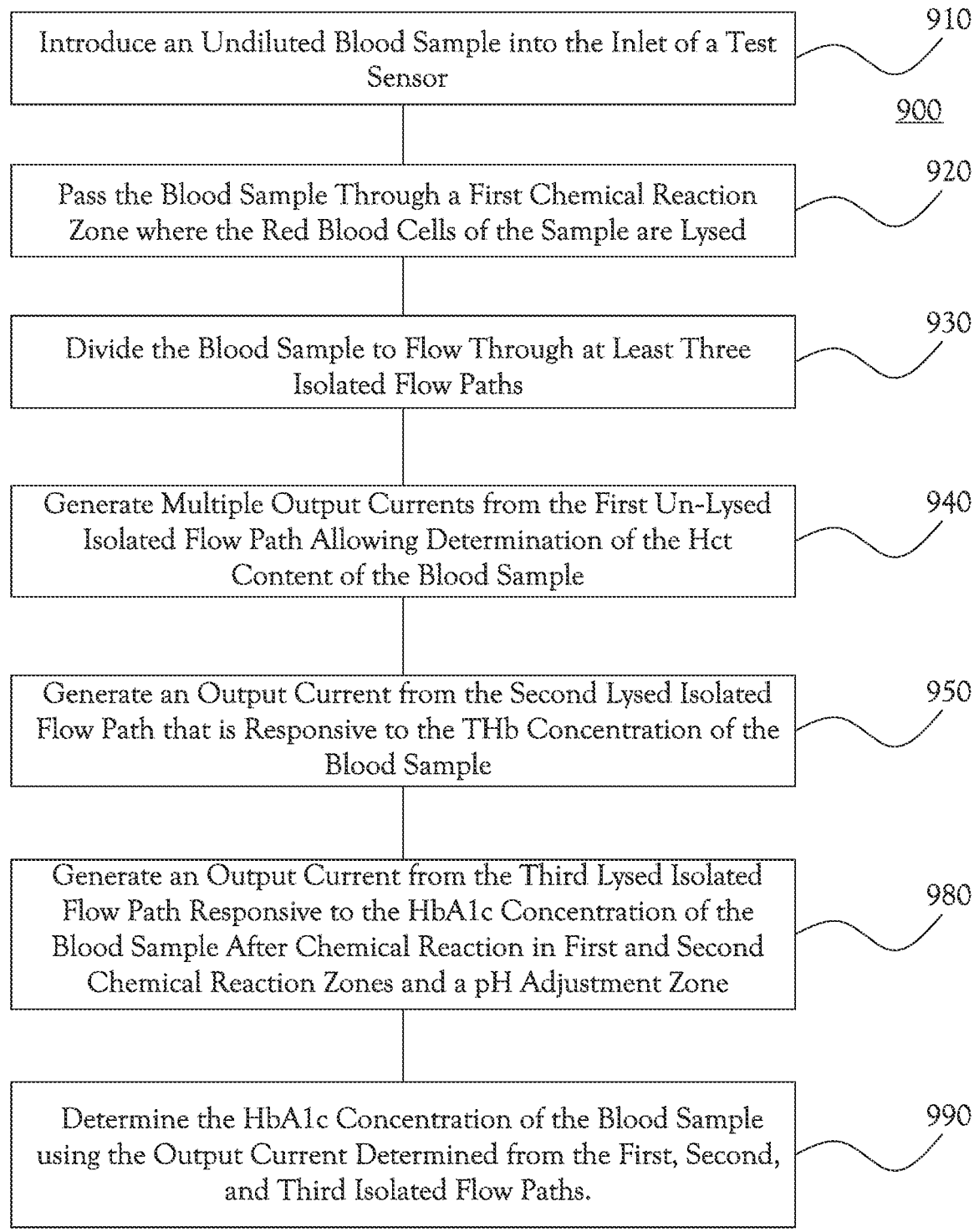
FIG. 9 represents a method of electrochemically determining the HbA1c content of an undiluted blood sample without correction that may be performed by the measurement device.

FIG. 9 represents a method 900 of electrochemically determining the HbA1c content of an undiluted blood sample without correction that may be performed by the measurement device 400 of FIG. 4A. In 910, an undiluted blood sample, such as taken from a vein or artery, is introduced to the inlet of a test sensor, such as the test sensor 300 of FIG. 3. In 920, the blood sample passes through a first chemical reaction zone where the red blood cells of the sample are lysed. In 930, the lysed blood sample is divided so it flows through two isolated flow paths. In first un-lysed flow path 940, multiple output currents are generated allowing determination of the Hct content of the blood sample. In second isolated flow path 950, an output current is generated that is responsive to the THb concentration of the blood sample. In third lysed flow path 980, an output current is generated that is responsive to the HbA1c concentration of the blood sample after chemical reaction in first and second chemical reaction zones and pH adjustment. In 990, the measurement device determines the HbA1c concentration of the blood sample using the output currents determined from the first, second, and third isolated flow paths. This analysis is unlikely to have the accuracy and/or precision of the method 800 of FIG. 8.

The following examples are provided to illustrate one or more preferred embodiments of the invention. Numerous variations can be made to the following examples that lie within the scope of the invention.

EXAMPLES

Example 1: Preparation of a First Chemical Reaction Zone including an Immobilized Lysing Matrix and an Interference Reduction Matrix Buffer Preparation: Ches Buffer-Sigma C2885 and Trizma Buffer-Sigma T1503 were used, with the Ches buffer being preferred. In one instance, 10.4 grams of Ches Buffer was added to 400 mL of distilled water and dissolved by stirring. The pH was adjusted 8.2 to provide a total solution volume of 500 mL.

Lysing Reagent and Interference Reduction Matrix Reagents: Poly(ethylene glycol) (PEG) m.w. 6000-Sigma S81260, 2-Hydroxyethyl cellulose 250 G (HEC)—Ashland Inc. Covington, KY., Saponin-Sigma 558255, Tetradecyltrimethylammonium bromide (TTAB)—Sigma T4762, Cetrimonium bromide (CTAB)—Sigma H9151, Ammonyx- LO-Stepan Co. Northfield, IL, Dess-Martin periodinane (Dess-Martin)-Sigma 274623, N-Ethylmaleimide (NEM)—Sigma-E1271, Sodium Azide-Sigma S2002, Avicel RC-591, Avicel Cl-611F,-FMC Health and Nutrition Philadelphia, PA, CaboSil 720-Cabot Corporation Boston, Massachusetts, Vinac XX-210-Ashland Inc. Columbus, Ohio, woven polyester mesh PES 18/13-Saarti, Saaticare PES 18/13, SaatiTech Somers, NY.

Lysing Reagent: One gram of the PEG was added to 90 mL of the Ches buffer solution and mixed until dissolved. Next, 0.5 grams of HEC was added to the solution and mixed until dissolved. Lysing agents for the matrix included: TTAB, CTAB, Ammonyx-Lo, and Saponin with Saponin being preferred. In the case of Saponin, 0.6 grams was added to the solution. The mixture was stirred for 2 hours to disperse the Saponin. The pH was adjusted to 8.0, and the total solution volume increased to 100 mL. The resulting mixture was sprayed on the top side of a polyester mesh.

Interference Reduction Matrix: One gram of PEG was added to 90 mL of the Ches buffer and stirred until dissolved. Next, 0.5 grams of HEC was added to the solution and stirred until dissolved. Next, 0.2545 grams of Dess-Martin, 0.0375 NEM, and 0.5 grams of Sodium Azide were added and stirred. While stirring 0.05 grams CaboSil 720, 0.10 grams of Avicel Cl-611F, and 0.125 grams of Vinac XX-210 were added. The mixture was homogenized. Then, 0.20 grams of Avicel RC-591 was added and the mixture was again homogenized. The resulting mixture was sprayed on the bottom side of the polyester mesh.

Example 2: Preparation of a Second Chemical Reaction Zone Including a Protein Cleaving Reagent Protein Cleaving Reagent: Trizma—Sigma t4661, Polyvinylpyrrolidone (PVP)—Sigma PVP40, Polyvinyl alcohol (PVA)—Sigma P8136, Avicel Cl-611F,-FMC Health and Nutrition Philadelphia, Vinac XX-210-Ashland Inc. Columbus, Ohio, PA Neutral Protease-NEP201 Toyobo Osaka, Japan, Polyester woven mesh 255 micron/40% open area (mesh)—Sefar Heiden Switzerland.

Preparation of 200 mM Trizma buffer solution: About 12 grams of Trizma buffer was added to 400 mL of distilled water and mixed until dissolved. The pH of the resulting solution was adjusted to a pH of 8.5 and a total volume of 500 mL.

Preparation of Polymer Solution: About 0.5 grams of PVP 40K and 1.5 grams of PVA was added to 90 mL of the previously prepared Trizma buffer and heated with agitation. One gram of Avicel Cl-611F and 0.5 grams of Vinac XX-210 were then added. The pH was adjusted to 8.50 to provide a liquid volume of 100 ml and homogenized.

Enzyme stock solution: Protein cleaving reagents include trypsin, and Papain with Neutral Proteinase being preferred. Assuming an enzyme activity of 1000 units/mg and 4 units per sensor, 0.04 grams of protease enzyme was added to 10 mL of the polymer solution. Mix until the enzyme is dissolved in the solution. A polyester mesh was then dipped into enzyme solution and dried at 45° C. for about 20 minutes.

Mesh Placement: The polymer mesh was positioned in the HbA1c channels after the lysing and interference reduction mesh, but before the pH adjustment zone and the FAOX coated reaction zone.

Example 3: Preparation of a pH Adjustment Zone

The pH of the sample lysate/proteolytic product flowing from the protease cleaving mesh matrix is about 7.5 to 9.0. This pH was adjusted to a pH compatible with the pH of the FAOX enzyme in the reaction zone.

A 200 mM Trizma buffer solution was prepared with Trizma Buffer—Sigma t4661—by adding about 12 grams of the Trizma Buffer to 400 mL of distilled water and stirring until dissolved. The pH was adjusted to 7.5 at a total solution volume of 500 mL. About 0.5 grams of HEC was added to the solution and stirred during which time 0.05 grams CaboSil 720, 0.10 grams of Avicel Cl-611F, and 0.125 grams of Vinac XX-210 were added. The mixture was homogenized, and the pH adjusted to 8.0.

Polymer dispense: A Biodot PixSys 3200 dispenser was used to dispense 2 uL of the mixture in the region downstream of the second chemical reaction zone, but before the electrical reaction zones. The test sensors were then dried at 45° C. for about 15 minutes.

Example 4: Preparation of an HbA1c Electrical Reaction Zone

Preparation of Phosphate Saline Buffer Solution: NaCl—Sigma S7653, KCl—Sigma P9333, $Na_2HPO_4.7H_2O$—Sigma 431478, $KH_2PO_4$ Sigma—P5655. Approximately 2 grams of NaCl, 0.05 g of KCl, 3.486 g of $Na_2HPO_4$, and 1.633 g of $KH_2PO_4$ was added to 800 mL distilled water and mixed until dissolved. The solution pH was adjusted to approximately 6.9 and additional water was added to bring the total volume to 500 mL.

Reagents for Fructosyl-amino acid oxidase Stock Solution: Polyvinylpyrrolidone (PVP)—Sigma PVP40, Polyvinyl alcohol (PVA)—Sigma P8136, Triton X 100—Sigma X100, Thesit—Sigma 88315, Fructosyl-amino acid oxidase (FAOX)—Toyobo Co. FPO-301

Approximately 0.5 grams of PVP 40K and 1 gram of PVA was added to 90 mL of the phosphate saline buffer solution and heated. Approximately 0.05 grams of Triton X-100, and 0.0033 grams of Thesit was added to the mixture and the mixture was agitated. Additional buffer was added to bring the total volume to 100 mL to provide a polymer solution. Assuming an enzyme activity of 5.4 units/mg., approximately 0.74074 grams of enzyme was then added to 5 mL of the polymer solution. The solution was mixed until the enzyme was dissolved. A Biodot PixSys 3200 dispenser (Biodot Inc. Irvine California) was used to dispense approximately 5 uL of the liquid in a line over the desired electrical reaction zones of the test sensor. The test sensors were dried at 45° C. for approximately 15 minutes and stored in a desiccator.

Example 5: Preparation of a THb Electrical Reaction Zone

Reagents: Saponin-Sigma 558255, Tetradecyltrimethylammonium bromide (TTAB)—Sigma T4762, Cetrimonium bromide (CTAB)—Sigma H9151, Ammonyx-LO-Stepan Co. Northfield, IL, Potassium hexacyanoferrate (III) (K3Fe(CN) 6)—Sigma 393517, Polyvinyl alcohol (PVA)—Sigma P8136, KCl-Sigma P9333, Triton X 100-Sigma-Aldrich X100.

Approximately 10.4 grams of Ches Buffer was added to 400 mL of distilled water and stirred until dissolved. The pH of the solution was adjusted to 9.0 and the total solution volume to 500 mL with distilled water. Approximately two grams of PVA was added to 90 mL of the Ches buffer solution. The solution was heated and mixed to dissolve the PVA. Then, about 0.15 grams KCl, about 1.6 grams of $K_3Fe(CN)_6$, and about 0.25 grams of Triton x-100 was added to the PVA/buffer solution and mixed. Then, about 0.6 grams of Saponin was added to the PVA/buffer solution and stirred for about two hours to disperse the Saponin. The pH was adjusted to 9.0 and the liquid volume to 100 mL with the Ches buffer. A Biodot PixSys 3200 dispenser (Biodot Inc. Irvine California) was used to dispense 5 uL of the liquid in a line over the desired electrical reaction zones of the test sensor. The test sensors were dried at 45° C. for approximately 15 minutes and stored in a desiccator.

Prophetic Example 6: HbA1c Analysis of an Undiluted Blood Sample with a Three-Analysis-Path Test Sensor A sample of whole blood is introduced into the inlet of a three-analysis-path test sensor, such as represented in FIG. 3. The sample divides and enters the isolated flow paths for Hct, THb, and HbA1c analysis. Upon determining sample presence or being notified to start the analysis and applying a potential to heat the desired reaction zones, the measurement device applies at least one potential to the working and counter electrodes of the Hct, THb, and HbA1c electrical reaction zones. The measurement device then determines the output current from each of the electrode pairs.

The measurement device determines the THb concentration from comparing the recorded current to a THb reference correlation. The measurement device determines the HbA1c concentration from comparing the recorded current to an HbA1c reference correlation. From these determinations, the measurement device determines the percent HbA1c in the whole blood sample.

The measurement device corrects the percent HbA1c in view of the Hct output current by selecting a predetermined HbA1c reference correlation, calculating a correction factor for the determined HbA1c concentration, or calculating a correction factor for the percent HbA1c concentration. The measurement device then displays the corrected percent HbA1c concentration of the whole blood sample.

Prophetic Example 7: HbA1c Analysis of an Undiluted Blood Sample with a Five-Analysis-Path Test Sensor A sample of whole blood is introduced into the inlet of a five-analysis-path test sensor, such as represented in FIG. 1. The sample divides and enters the isolated flow paths for Hct, THb, HbA1c, electrochemical background, and endogenous background HbA1c analysis. Upon determining sample presence or being notified to start the analysis and applying a potential to heat the desired reaction zones, the measurement device applies at least one potential to the working and counter electrodes of the Hct, THb, HbA1c, electrochemical background, and endogenous background HbA1c electrical reaction zones. The measurement device then determines the output current from each of the electrode pairs.

The measurement device determines the THb concentration from comparing the recorded current to a THb reference correlation. The measurement device determines the HbA1c concentration from comparing the recorded current to an HbA1c reference correlation.

The measurement device modifies the HbA1c concentration in view of the output currents determined from the electrochemical background and endogenous background HbA1c electrical reaction zones. The HbA1c concentration can be modified by modifying the determined current from the HbA1c electrical reaction zone before the current is converted into a HbA1c concentration or by modifying the determined HbA1c concentration. From these determinations, the measurement device determines the percent HbA1c in the whole blood sample.

The measurement device corrects the percent HbA1c in view of the Hct output current by selecting a predetermined HbA1c reference correlation, calculating a correction factor for the determined HbA1c concentration, or calculating a correction factor for the percent HbA1c concentration. The measurement device then displays the corrected percent HbA1c concentration of the whole blood sample.

Example 8: Comparison of Described Biosensor System Determined Verses Reference Determined HbA1c Sample Analyte Concentrations Multiple whole blood samples were tested for percent HbA1c with a reference system and with the described biosensor system. The results were as follows:

TABLE 1

| Sample | Reference Instrument | Described Biosensor System |
| --- | --- | --- |
| 1 | 4.7 | 4.7 |
| 2 | 4.9 | 6.6 |
| 3 | 5.7 | 5.53 |
| 4 | 5.9 | 6.2 |
| 5 | 7 | 6.3 |
| 6 | 7.3 | 9.1 |
| 7 | 10 | 9.0 |
| 8 | 10.5 | 8.24 |
| 9 | 12.2 | 10.6 |
| 10 | 12.5 | 11.5 |
| 11 | 13.6 | 15.0 |
| 12 | 15.9 | 17.1 |

These results established that the described biosensor system was able to provide percent HbA1c % determinations from undiluted blood samples relatively close to those determined with a benchtop reference instrument. While the values determined with the described biosensor system are not identical, the correlation has a greater than $R^2$ of 0.9. Considering the variances in sample handling and analysis conditions, the correlation was greater than expected.

To provide a clear and more consistent understanding of the specification and claims of this application, the following definitions are provided.

An undiluted blood sample is a blood sample that has not been pre-treated or otherwise diluted after collection but before introduction to the test sensor for analysis. Collection may be through phlebotomy, finger-stick, and the like depending on the volume of undiluted blood required for the analysis.

A biosensor system is the combination of a measurement device and a test sensor for analyzing one or more analytes in a sample.

A reference correlation is a predetermined correlation between output currents from the biosensor system and samples having known characteristics of interest. Thus, a line or curve may be generated at a known temperature between multiple samples having known concentrations of a specific species (such as HbA1c, THb, Hct, and the like) and the corresponding output current generated from the measurement device in response to an input from the measurement device. While "output current" or "current" are used throughout the application for convenience, these terms are intended to include voltage and/or amperage. The reference correlation is then stored in the measurement device for later use during the analysis. The reference correlation between known sample analyte concentrations and output current values from the measurement device may be represented graphically, mathematically, a combination thereof, or the like in the measurement device. Reference correlations may be represented by a program number (PNA) table, another look-up table, or the like that is predetermined and stored in the measurement device of the biosensor system. The latter analysis of the sample by the biosensor system transforms an output current determined by the measurement device into the concentration of the specific species in the sample using the previously determined reference correlation stored in the measurement device.

A chemical reaction zone includes one or more chemical or biochemical reagents that react with one or more constituents of the sample.

An electrical reaction zone has the ability to apply an electric potential or voltage to the sample using at least two electrodes. The current generated by the applied potential may be responsive to an electrochemical reaction of one or more constituents in the sample, the conductivity of the sample or the like. Thus, an electrical reaction zone can cause an electrochemical reaction, but may not depending on the reagents in the sample.

An "independent potential" in the context of an electrode means that the electrode includes both species of a redox pair, which can provide a potential during the analysis. A common conductive material having an independent potential is silver/silver chloride (Ag/AgCl) with silver metal serving as the oxidizable species of the redox pair and the silver chloride salt serving as the reducible species of the redox pair. Both redox species of the redox pair of a redox reagent also may be present on or near an electrode material, such as carbon or platinum, to provide an independent potential to the electrode. A common redox reagent for providing an independent potential is a mixture of ferricyanide, the reducible redox species, and ferrocyanide, the oxidizable redox species of the redox pair. The potential provided by the redox reagent may be altered by the reduction potential of the selected redox reagent, the ratio of each species of the redox pair, and the area of the redox reagent exposed to the sample. Such an independent potential material or redox reagent when used as a counter electrode can function as a "pseudo-reference electrode" in the absence or in addition to an independent reference electrode. The reference or pseudo-reference electrode can provide a known independent potential in response to an applied potential during the analysis.

Redox reagents include one or more species of a redox pair that may undergo oxidation and reduction. Redox reagents may include ferricyanide ($FeCN_6$), ferrocene, Prussian Blue, metal phthalocyanine, tetrathiafulvalene (TTF), and other chemical moieties capable of undergoing oxidation or reduction to assist in electron transport. Preferably, redox reagents are selected on the basis of redox potential and chemical compatibility with the analysis.

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a material over its top surface, yet a second element over at least a portion of the first element and its top material can be described as "on" the first element. Thus, the use of the term "on" may or may not mean that the two elements being related are in physical contact with each other.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. A method of determining a corrected glycated hemoglobin concentration of an undiluted whole blood sample, the method comprising:
   introducing an undiluted whole blood sample to a test sensor;
   applying a potential to at least two electrical conductors of a hematocrit flow path;
   determining an output current responsive to a hematocrit content of the sample;
   applying a potential to a total hemoglobin working and counter electrode pair;
   determining an output current from the total hemoglobin working and counter electrode pair responsive to a total hemoglobin concentration of the sample;
   applying a potential to a glycated hemoglobin working and counter electrode pair;
   determining an output current from the glycated hemoglobin working and counter electrode pair responsive to a glycated hemoglobin concentration of the sample; and
   determining a corrected glycated hemoglobin concentration of the sample from the output currents, the output currents determined from
   the hematocrit flow path,
   the total hemoglobin working and counter electrode pair, and
   the glycated hemoglobin working and counter electrode pair.

2. The method of claim 1, where the applying the potential to at least two electrical conductors of the hematocrit flow path includes applying the potential to at least four electrical conductors of the hematocrit flow path and the determining the output current responsive to the hematocrit content of the sample includes determining at least three timing values from the at least four electrical conductors, the at least three timing values responsive to an entry rate of the sample through the test sensor.

3. The method of claim 2, further comprising determining a value responsive to sample viscosity from the at least three timing values.

4. The method of claim 1 where the applying the potential to at least two conductors of the hematocrit flow path includes applying the potential to a hematocrit working and counter electrode pair and the determining the output current responsive to the hematocrit content of the sample includes determining an output current from the hematocrit working and counter electrode pair.

5. The method of claim 4, where the output current determined from the hematocrit working and counter electrode pair is responsive to the electrical conductivity of the sample.

6. The method of claim 1, further comprising before applying the potential to the total hemoglobin working and counter electrode pair, contacting the sample with a first chemical reaction zone and a pH adjustment zone.

7. The method of claim 6, where the contacting the sample with the first chemical reaction zone lyses red blood cells in the sample and reduces lysate interference in the corrected glycated hemoglobin concentration determined from the sample.

8. The method of claim 6, where the contacting the sample with the pH adjustment zone alters the pH of the sample.

9. The method of claim 1, further comprising before applying the potential to the glycated hemoglobin working and counter electrode pair, contacting the sample with a first chemical reaction zone, a second chemical reaction zone, a pH adjustment zone, and an enzyme.

10. The method of claim 9, where the contacting the sample with the second chemical reaction zone reduces the length of at least one peptide chain in the sample.

11. The method of claim 1, where the contacting the sample with the enzyme produces an electrochemically active species having a concentration in the sample responsive to a glycated hemoglobin concentration of the sample.

12. The method of claim 1, further comprising heating the total hemoglobin working and counter electrode pair and the glycated hemoglobin working and counter electrode pair to a temperature from 35 to 54 degrees Celsius before applying the potential to the total hemoglobin working and counter electrode pair and the glycated hemoglobin working and counter electrode pair, respectively.

13. The method of claim 1, further comprising
applying a potential to an electrochemical background working and counter electrode pair;
determining an output current from the electrochemical background working and counter electrode pair responsive to an electrochemical background of the sample, where the determining the corrected glycated hemoglobin concentration of the sample from the output currents includes at least one current determined from the electrochemical background working and counter electrode pair.

14. The method of claim 13, further comprising before applying the potential to the electrochemical background working and counter electrode pair, contacting the sample with a first chemical reaction zone, a second chemical reaction zone, and a pH adjustment zone.

15. The method of claim 13, where the electrochemical background working and counter electrode pair lack an enzyme capable of producing an electrochemically active species.

16. The method of claim 13, further comprising heating the electrochemical background working and counter electrode pair to a temperature from 35 to 54 degrees Celsius before applying the potential to the electrochemical background working and counter electrode pair.

17. The method of claim 1, further comprising
applying a potential to an endogenous glycated hemoglobin background working and counter electrode pair;
determining an output current from the endogenous glycated hemoglobin background working and counter electrode pair responsive to an endogenous glycated hemoglobin background of the sample, where the determining the corrected glycated hemoglobin concentration of the sample from the output currents includes at least one current determined from the endogenous glycated hemoglobin background working and counter electrode pair.

18. The method of claim 17, further comprising before applying the potential to the endogenous glycated hemoglobin background working and counter electrode pair, contacting the sample with a first chemical reaction zone, a pH adjustment zone, and an enzyme.

19. The method of claim 17, further comprising heating the endogenous glycated hemoglobin working and counter electrode pair to a temperature from 35 to 54 degrees Celsius before applying the potential to the endogenous glycated hemoglobin background working and counter electrode pair.

20. The method of claim 18, where the contacting the sample with the enzyme produces an electrochemically active species having a concentration in the sample responsive to a glycated hemoglobin concentration of the sample.

21. The method of claim 1, where the determining the corrected glycated hemoglobin concentration of the sample includes determining a percent glycated hemoglobin to total hemoglobin value from the output currents determined from the glycated hemoglobin working and counter electrode pair and the total hemoglobin working and counter electrode pair, respectively.

22. The method of claim 21, where the determining the corrected glycated hemoglobin concentration of the sample includes correcting the percent glycated hemoglobin to total hemoglobin value with the output currents determined from the hematocrit flow path.

* * * * *